(12) United States Patent
Kaduchak et al.

(10) Patent No.: US 10,520,418 B2
(45) Date of Patent: Dec. 31, 2019

(54) SYSTEMS AND METHODS FOR DIAGNOSING A FLUIDICS SYSTEM AND DETERMINING DATA PROCESSING SETTINGS FOR A FLOW CYTOMETER

(71) Applicant: LIFE TECHNOLOGIES CORPORATION, Carlsbad, CA (US)

(72) Inventors: Gregory Kaduchak, Chandler, AZ (US); Jace Akerlund, Eugene, OR (US); Jason Malkin, Eugene, OR (US); Michael Ward, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 81 days.

(21) Appl. No.: 15/984,695

(22) Filed: May 21, 2018

(65) Prior Publication Data
US 2018/0335375 A1   Nov. 22, 2018

Related U.S. Application Data

(62) Division of application No. 14/612,820, filed on Feb. 3, 2015, now Pat. No. 10,001,434.
(Continued)

(51) Int. Cl.
*G06F 11/30* (2006.01)
*G01N 15/10* (2006.01)
*G01N 15/14* (2006.01)

(52) U.S. Cl.
CPC ..... *G01N 15/1012* (2013.01); *G01N 15/1404* (2013.01); *G01N 15/1429* (2013.01); *G01N 15/1434* (2013.01); *G01N 15/1459* (2013.01); *G01N 2015/1018* (2013.01); *G01N 2015/1068* (2013.01); *G01N 2015/1075* (2013.01); *G01N 2015/1438* (2013.01)

(58) Field of Classification Search
CPC .................................. G01N 15/1012
See application file for complete search history.

(56) References Cited

U.S. PATENT DOCUMENTS
10,001,434 B2   6/2018   Kaduchak et al.

FOREIGN PATENT DOCUMENTS
| EP | 0737855 | 10/1996 | |
| EP | 0737855 A1 * | 10/1996 | ............. G01N 15/14 |

(Continued)

OTHER PUBLICATIONS
PCT/US2015/014210, "International Preliminary Report on Patentability dated", Sep. 15, 2016, 10 pp.
(Continued)

*Primary Examiner* — Phuong Huynh
(74) *Attorney, Agent, or Firm* — BakerHostetler

(57) ABSTRACT

The present set of embodiments relates to systems and methods for diagnosing a fluidics system and determining data processing settings for a flow cytometer. Systems and methods for diagnosing a fluidics system require accurate measurement and interpretation of fluctuations within the fluid delivery system. Systems and methods for determining data processing settings require an accurate measurement of peak times among various channels and being able to adjust time delay settings wherein peak time is the measurement of time elapsed from the beginning of the data collection time window to the highest peak in the window.

20 Claims, 24 Drawing Sheets

Related U.S. Application Data

(60) Provisional application No. 62/056,646, filed on Sep. 29, 2014, provisional application No. 61/948,547, filed on Mar. 6, 2014.

(56) References Cited

FOREIGN PATENT DOCUMENTS

| | | | |
|---|---|---|---|
| WO | WO-2011/112697 | 9/2011 | |
| WO | WO-2011112697 A1 * | 9/2011 | ......... G01N 15/1427 |
| WO | WO-2013/028947 | 2/2013 | |

OTHER PUBLICATIONS

PCT/US2015/014210, "International Search Report and Written Opinion dated ", Apr. 14, 2015, 13 pgs.

* cited by examiner

SYSTEMS AND METHODS FOR DIAGNOSING A FLUIDICS SYSTEM AND DETERMINING DATA PROCESSING SETTINGS FOR A FLOW CYTOMETER

CROSS-REFERENCE TO RELATED APPLICATIONS

This application is a divisional of U.S. application Ser. No. 14/612,820 filed Feb. 3, 2015, now U.S. Pat. No. 10,001,434, and claims priority to U.S. application No. 61/948,547 filed Mar. 6, 2014, and U.S. application No. 62/056,646 filed Sep. 29, 2014, which disclosures are herein incorporated by reference in their entirety.

FIELD

The present disclosure generally relates to fluidic systems in the field of flow cytometry and more specifically to systems and methods for diagnosing fluidics failures and setting data acquisition and analysis settings.

BACKGROUND

Flow cytometry is a powerful tool used for analysis of particles and cells in a myriad of applications primarily in bioscience research and medicine. The analytical strength of the technique is in its ability to parade single particles (including bioparticles such as cells, bacteria and viruses) through the focused spot of light sources, typically a laser or lasers, in rapid succession, at rates up to tens of thousands of particles per second. The high photon flux at this focal spot produces scatter of light by a particle and or emission of light from the particle or labels attached to the particle that can be collected and analyzed. This gives the user a wealth of information about individual particles that can be quickly parleyed into statistical information about populations of particles or cells.

In traditional flow cytometry, particles are flowed through the focused interrogation point where a laser directs a laser beam to a focused point that includes the core diameter within the channel. The sample fluid containing particles is focused to a very small core diameter of around 5-50 microns by flowing sheath fluid around the sample stream at a very high volumetric rate on the order of 100-1000 times the volumetric rate of the sample. This results in very fast linear velocities for the focused particles on the order of meters per second. This in turn means that each particle spends a very limited time in the excitation spot, often only 1-10 microseconds.

In a conventional flow cytometer there are analytical tools and/or methods needed to track full system and subsystem performance. Subsystems that can fail in a flow cytometer can include optics, electronics, and fluidics either independently or collectively. Traditionally, flow cytometry data acquisition and/or diagnostics software comes with a mode for measuring the immediate system performance and comparing it with a previous day(s) performance. These performance tests often use a cocktail of beads with known fluorescent characteristics. The performance test will use these beads to make a series of measurements including coefficient of variation of a population of 'bright' fluorescent beads, optical background, and quantum efficiency of the detection channel. By monitoring these values and how they change, it can be determined when an instrument is no longer functioning within specification and should be serviced. The person servicing the instrument may run tests on the optics, electronics, and fluidics; the failure mode is then determined through process of elimination or isolation of variables.

Unfortunately, one of the biggest difficulties in servicing flow cytometers is that most measured parameters are derived from convoluted inputs of the optics, electronics, and fluidic systems. Techniques for isolation of many optical and electronic components exist. Due to the microfluidic nature of the fluidic system, very few sensors and tests are available to isolate and determine the health and/or accurately measure the flow profile of the fluid delivery system. For this reason, optics and electronics are tested and only if the problem isn't solved is the fluidic system tested. Beyond measuring steady-state pressure or investigating for leaks, testing of fluidics usually includes swapping in and out various components in the hopes of finding solutions. Flow cytometers with multiple laser beams are especially sensitive to pressure fluctuations within the fluid delivery system with fluctuations well below 1% of the total operating pressure causing coefficient of variation broadening in the optical data. In this situation a person would be called to fix the coefficient of variation broadening in the optical data and the testing begins at the optical and electronic interfaces.

As such, there is a need to be able to detect steady state and dynamic irregularities or failures in the fluidic systems for flow cytometers in isolation, to decouple fluidics from optical and electronic subsystems without having to run failed experiments and then troubleshoot various subsystems before the fluidics system can even be considered. Such a detection system can be used for both troubleshooting a broken fluidic systems as well as helping adjust a working fluidic system to meet the intended specifications.

BRIEF SUMMARY

In one aspect, a method for determining data processing settings for a flow cytometer is disclosed. The method can include passing a set of calibration particles through a flow cell. The method can include illuminating each of the set of calibration particles passing through the flow cell with at least two light beams wherein each light beam is associated with a channel. The method can include collecting light emitted from each of the set of calibration particles using a detector associated with each channel. The method can include recording data from each detector. The method can include setting a trigger channel to initiate a transfer of data from a first data collection time window associated with the trigger channel when a data signal threshold for the trigger channel is exceeded. The method can include setting a second channel to transfer data from a second data collection time window associated with the second channel when the data signal threshold for the trigger channel is exceeded, and wherein the start of the second data collection time window is based on a spatial path between the trigger channel and the second channel. The method can include recording data from the first data collection time window to a data store each time the data signal threshold is exceeded. The method can include recording data from the second data collection time window to the data store each time the data signal threshold for the trigger channel is exceeded. The method can include analyzing a distribution of data intensity peak times within the second data collection time window. The method can include calculating a time delay based on the distribution of data intensity peak times in the second data collection time window to position a data signal in the second channel in the second data collection time window. The method can include the light emitted being fluorescent.

The method can include the light emitted being scattered. The method can include the start of the second data collection time window is based on a flow rate. The method can include the start of the second data collection time window is based on a sheath fluid flow rate. The method can include the spatial path being between about 80 to 250 micrometers. The method can include the spatial path being about 150 micrometers. The method can include the data collection time windows being between about 80 to about 120 ADC points wide. The method can include the data collection time windows being between about 320 to about 360 ADC points wide.

In one aspect, a system to determine data processing settings for a flow cytometer is disclosed. The system can include a flow cell configured to flow calibration particles. The system can include at least two light sources each configured to emit a light beam, wherein each light beam is associated with a channel and, wherein the light beams pass through the flow cell. The system can include a detector associated with each channel wherein each detector can be configured to collect light emitted from each of the set of calibration beads. The system can include a memory buffer configured to record data from each of the detectors. The system can include a trigger channel configured to initiate a transfer of data from a first data collection time window associated with the trigger channel when a data signal threshold for the trigger channel is exceeded. The system can include a second channel configured to transfer data from a second data collection time window associated with the second channel when the data signal threshold for the trigger channel is exceeded wherein the start of the second data collection time window is based on a spatial path between the trigger channel and second channel. The system can include a trigger processor configured to transfer the data from the first data collection time window to a data storage each time the data signal intensity threshold is exceeded and transfer the data from the second data collection time window to the data storage each time the data signal intensity threshold is exceeded. The system can include a computer processor configured analyze a distribution of data intensity peak times within the second data collection time window and calculate a time delay based on the distribution of data intensity peak times in the second data collection time window to position a data signal in the second channel in the second data collection time window. The system can include a field programmable gate array wherein the memory buffer and the trigger processor are subcomponents of a field programmable gate array. The system can include the light emitted being fluorescent. The system can include the light emitted being scattered. The system can include the start of the second data collection time window being based on a flow rate. The system can include the start of the second data collection time window being based on a sheath fluid flow rate. The system can include the spatial path being between about 80 to 250 micrometers. The system can include the spatial path being about 150 micrometers. The system can include the data collection time windows being between about 80 to about 120 ADC points wide. The system can include the data collection time windows being between about 320 to about 360 ADC points wide. In one aspect, a fluidic diagnostic method for a flow cytometer is disclosed. The method can include passing a set of calibration particles through a flow cell. The method can include illuminating each of the set of calibration particles passing through the flow cell with at least two light beams wherein each light beam is associated with a channel. The method can include collecting light emitted from each of the set of calibration particles using a detector associated with each channel. The method can include recording data from each of the detectors. The method can include setting a trigger channel to initiate a transfer of data from a first data collection time window associated with the trigger channel when a data signal threshold for the trigger channel is exceeded. The method can include setting a second channel to transfer data from a second data collection time window associated with the second channel when the data signal threshold for the trigger channel is exceeded. The method can include recording data from the first data collection time window to a data store each time the data signal threshold is exceeded. The method can include recording data from the second data collection time window to the data store each time the data signal threshold for the trigger channel is exceeded. The method can include analyzing a distribution of data intensity peak times within the second data collection time window and comparing the distribution to a system specification to determine the health of a fluidics system. The method can include the system specification being 1 standard deviation. The method can include the system specification being 2 standard deviations. The method can include the system specification being 3 standard deviations. The method can include the system specification being 4 standard deviations. The method can include the system specification being a Gaussian distribution. The method can include the system specification being a Poisson distribution. The method can include the system specification being any statistical distribution. The method can include the light emitted being fluorescent. The method can include the light emitted being scattered. The method can include the data collection time windows being between about 80 to about 120 ADC points wide. The method can include the data collection time windows being between about 320 to about 360 ADC points wide.

In one aspect a fluidic diagnostic system for a flow cytometer is disclosed. The system can include a flow cell configured to flow calibration particles. The system can include at least two light sources each configured to emit a light beam, wherein each light beam is associated with a channel and, wherein the light beams pass through the flow cell. The system can include a detector associated with each channel wherein each detector is configured to collect light emitted from each of the set of calibration beads. The system can include a memory buffer configured to record data from each of the detectors. The system can include a trigger channel configured to initiate a transfer of data from a first data collection time window associated with the trigger channel when a data signal threshold for the trigger channel is exceeded. The system can include a second channel configured to transfer data from a second data collection time window associated with the second channel when the data signal threshold for the trigger channel is exceeded. The system can include a trigger processor configured to transfer the data from the first data collection time window to a data storage each time the data signal intensity threshold is exceeded and transfer the data from the second data collection time window to the data storage each time the data signal intensity threshold is exceeded. The system can include a computer processor configured to compare a distribution of data intensity peak times within the second data collection time window to a system specification to determine the health of a fluidics system. The system can include a field programmable gate array wherein the memory buffer and the trigger processor can be subcomponents of the field programmable gate array. The system can include wherein the system specification being 1 standard deviation. The system can include the system specification being 2 standard deviations. The system can include the system specification being 3 standard deviations. The system can include the system specification being 4 standard deviations. The system can include the system specification being a Gaussian distribution. The system can include the system specification being a Poisson distribution. The system can include the system specification being any statistical distribution. The system can include the light emitted being fluorescent. The system can include the light emitted being scattered. The system can include the data collection time windows being between about 80 to about 120 ADC points wide. The system can include the data collection time windows being between about 320 to about 360 ADC points wide.

DETAILED DESCRIPTION

Figure 1:
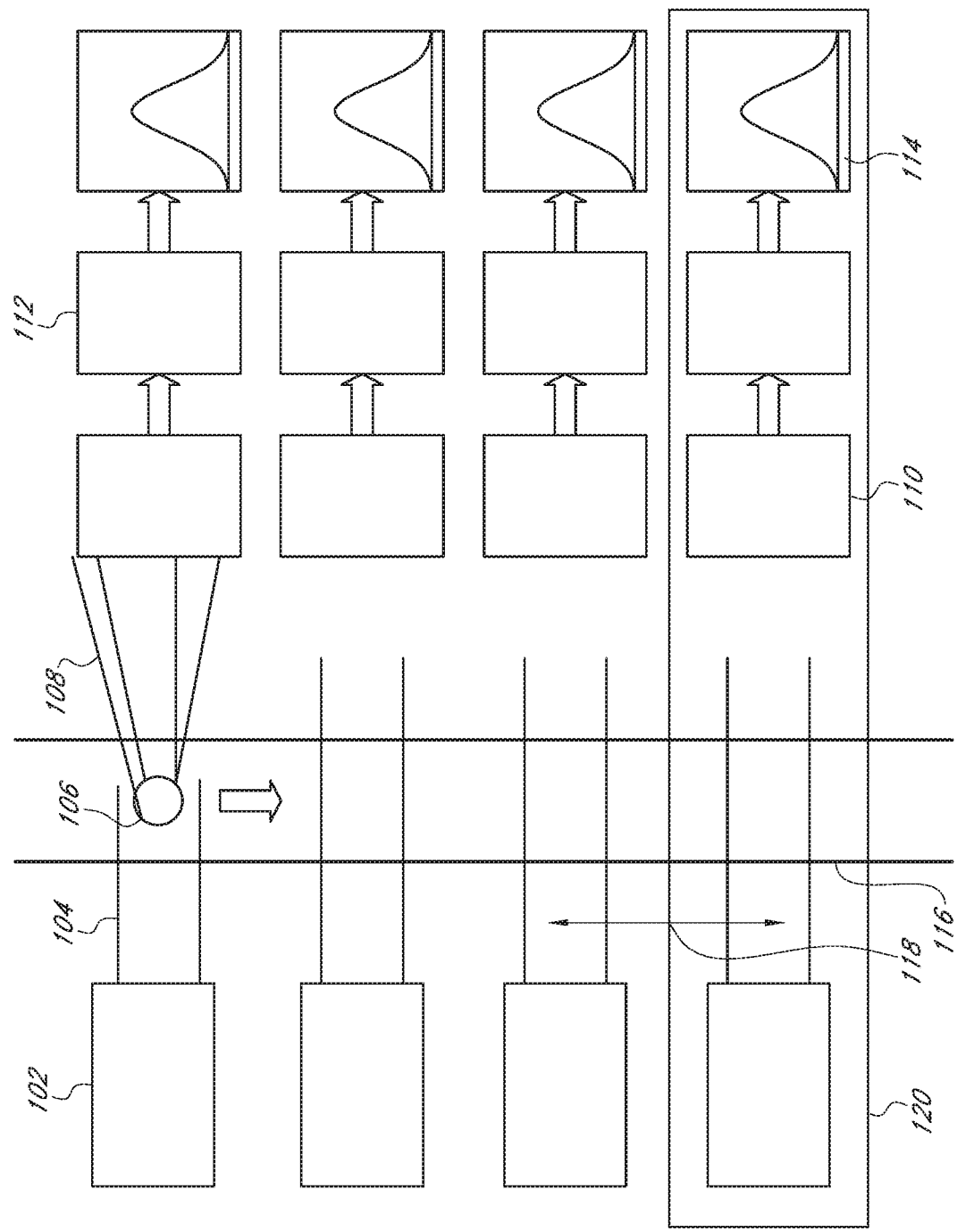
FIG. 1 is an illustration of one of various embodiments of a basic flow cytometer.

Embodiments of systems and methods for fluidic diagnostics and data collection and analysis settings for flow cytometers are described in the accompanying description and figures. In the figures, numerous specific details are set forth to provide a thorough understanding of certain embodiments. A person skilled in the artisan will be able to appreciate that the systems and methods described herein can be used in a variety of instruments using fluidic systems including, but not limited to, flow cytometers. Additionally, the skilled artisan will appreciate that certain embodiments may be practiced without these specific details. Furthermore, one skilled in the art can readily appreciate that the specific sequences in which methods are presented and performed are illustrative and it is contemplated that the sequences can be varied and still remain within the spirit and scope of certain embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

In order that the present disclosure may be more readily understood, certain terms are first defined. Additional definitions are set forth throughout the detailed description.

As used herein "ADC point" is the time interval between sampling points of the analog to digital converter. For the purpose of this specification, 1 ADC point can either be 500 nanoseconds or 1 microsecond.

As used herein "analyte" means a substance or material to be analyzed.

As used herein "channel" means a path through a flow cell where data collection occurs.

As used herein the term "diagnostic parameter" means qualities or measurements relating to laminar flow stability, mechanical perturbation arising in a pump or a gear pump, time between particles arriving (particle arrival time), fluid pressure, high fluid pressure, low fluid pressure, fluid pressure fluctuations, leaking, and/or anything known in the art that relates to fluidic systems qualities.

As used herein "flow cell" means a flow channel, a chamber or a capillary having an interior shape selected from rectangular, square, elliptical, oblate circular, round, octagonal, heptagonal, hexagonal, pentagonal, and trigonal.

As used herein "label" means an identifiable substance, such as a dye or a radioactive isotope that is introduced in a system, such as a biological system, and can be followed through the course of a flow cell or channel, providing information on the particles or targets in the flow cell or channel.

As used herein "microsphere" or "bead" means a particle that can be symmetric as in a sphere, asymmetric as in a dumbbell shape or a macromolecule having no symmetry. Examples of microspheres or beads include, but are not limited to, silica, glass and hollow glass, latex, silicone rubbers, polymers such as polystyrene, polymethylmethacrylate, polymethylenemelamine, polyacrylonitrile, polymethylacrylonitrile, poly(vinylidene chloride-co-acrylonitrile), and polylactide.

As used herein "particle" means a small unit of matter, to include but not limited to: biological cells, such as, eukaryotic and prokaryotic cells, archaea, bacteria, mold, plant cells, yeast, protozoa, ameba, protists, animal cells; cell organelles; organic/inorganic elements or molecules; microspheres; and droplets of immiscible fluid such as oil in water.

As used herein "peak" is relating to a high point in signal amplitude. In some cases, the signal can originate from fluorescence.

As used herein "peak time" is the measurement of time elapsed from the beginning of the data collection time window to the highest peak in the window.

As used herein "probe" means a substance that is labeled or otherwise marked and used to detect or identify another substance in a fluid or sample.

As used herein "reagent" is a substance known to react in a specific way.

As used herein "signaling molecule" means an identifiable substance, such as a dye or a radioactive isotope that is introduced in a system, such as a biological system, and can be used as a signal for particles.

As used herein "spatial separation" or "spatial separation between channels" means the distance from the center of one light beam to the center of the adjacent light beam.

As used herein "specification" means flow cytometer performance meeting a data quality requirement to meet the needs of an individual experiment.

As used herein "target" means a binding portion of a probe.

As used herein "transients" are temporary system instabilities that eventually stabilize. For example, an air bubble in a fluidics system that expands and contracts can cause a transient.

As used herein "trigger threshold" means the point where an intensity value from a signal is high enough to activate processing electronics in order to process a detected event.

As used herein "trigger" or "triggering" is the activation of processing electronics when an intensity value from a signal goes above the trigger threshold.

As used herein "trigger laser" or "trigger channel" is the set of hardware that is responsible for sensing a trigger threshold and indicating that all the acquired data coming from all the lasers or channels in the system needs to be stored and analyzed.

As used herein "window," "collection window," "data collection window," "data collection time window," "data analysis window" is the data that is initially analyzed by the digital sampling electronics for height, width, and area then is later transferred from a digital sampling electronics to a permanent storage location for further analysis.

In various embodiments, the systems, methods, and apparatuses disclosed in the present application can be used in conjunction with various apparatuses, systems, and methods relating to flow cytometry. See U.S. patent application Ser. Nos. 12/239,390 and 12/209,084, both of which are incorporated by reference in their entirety. Also see *Practical Flow Cytometry*, 4*th* Edition, Howard M. Shapiro, which is incorporated by reference in its entirety.

FIG. 1 is a basic illustration of a flow cytometer and the way in which data can be collected. Various embodiments can include at least one light source 102. Each of the light sources 102 can produce a light beam 104 which can then illuminate a particle 106 as the particle passes through a flow cell 116. The illumination can result in light 108 coming off of the particle. The form of light 108 can include fluorescent or scattered light. The light 108 can then be detected by a detector 110 and data 114 can be transferred to the digital sampling electronics 112. In various embodiments, the digital sampling electronics 112 can include memory of some kind which can be in an analog or digital form. Memory can be random access memory or a circular buffer that makes use of random access memory. In the digital sampling electronics 112 data 114 can be produced from the signal which can include height, width, and peak time information. The data 114 can be in the form of voltages and can be used in fluidic diagnostics and in calibrating time delay settings. In various embodiments, an analog to digital converter can be used to convert voltages into digital data. In various embodiments, images can be used instead of voltages and intensities can be extrapolated. Additionally, the spatial separation 118 (or spatial path) can be measured by the distance between adjacent light beams 104. There can be a spatial separation 118 between channels 120 which in various embodiments can be about 150 micrometers or in other various embodiments can be about 80 micrometers to about 250 micrometers. As used herein, a channel 120 can be a data collection path. In FIG. 1, there are four such data collection paths or channels 120 shown, however, various embodiments can use any number of channels 120.

In various embodiments the digital sampling electronics 112 can be analog sampling electronics or simple sampling electronics. In various embodiments, the digital sampling electronics 112 can include a field programmable gate array wherein the field programmable gate array can include a memory buffer, a trigger processor, and a calculation block. The memory buffer can store all data 114 and when a data signal intensity threshold (trigger threshold) is exceeded the data 114 can then be processed by the calculation block and sent to a computer. The computer can include memory, a processor, and any other components known in the art.

Figure 2:
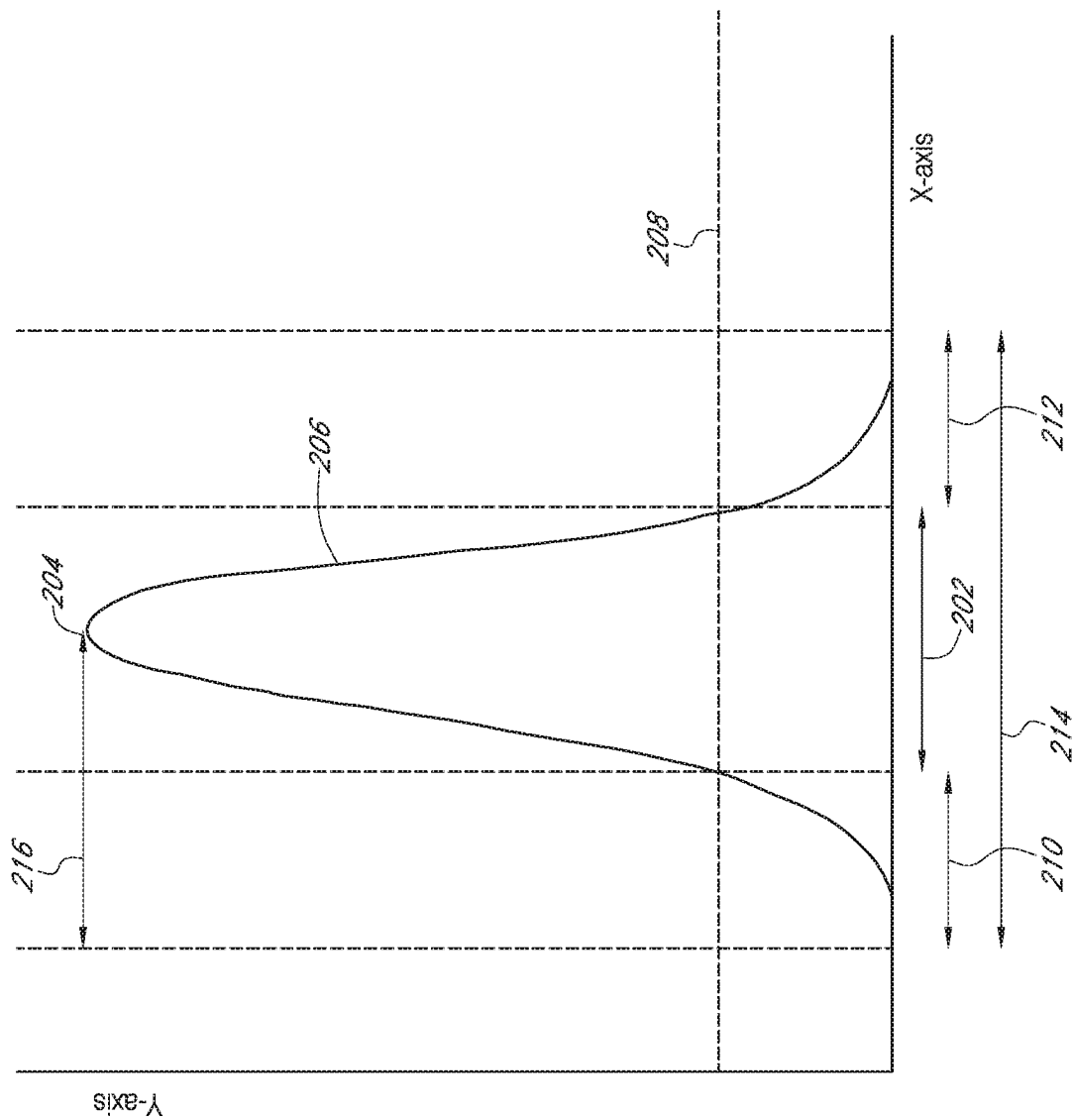
FIG. 2 is an illustration of one example of some of the types of data that can be collected by a flow cytometer.

FIG. 2 depicts an example illustration of resulting data 114 when it has been plotted to an x and y coordinate system and is displayed as a signal plot 206. The x-axis can represent time and the y-axis can represent signal intensity. In various embodiments, the signal intensity can originate from fluorescence intensity. In various embodiments, the intensity can be amplified in a photomultiplier tube or similar device and later measured in voltage. In various embodiments, when the signal intensity reaches a trigger threshold 208, the digital sampling electronics 112 can register that a particle (or event) has been detected and can perform some digital processing or transfer the data to permanent data storage, or do both. The permanent data storage can be located on a computer. In FIG. 2, a pulse width can be seen to include the width of the signal plot 206 at the trigger threshold 208. The highest peak 204 (also called data intensity peak or pulse height) can be where the signal plot is at its highest in relation to the y-axis. Generally, when setting the data collection time window 214 there is incentive to collect as much of the relevant data 114 as possible. Therefore, the data collection time window 214 can include the pulse width 202 as well as a front extension 210 and a rear extension 212. The data collection time windows 214 can be set prior to an experiment and with the consideration that the location of signal plots 206 are likely to have some variance.

The data collection time windows 214 can be dynamic and set during an experiment on a particle-by-particle basis. When deciding a final data time collection window 214 size several considerations become relevant. The data time collection window 214 cannot be too large or there is a risk of coincidence and the data time collection window 214 cannot be too small or data from a particle 106 will fall outside the boundaries of the data time collection window 214.

Figure 3:
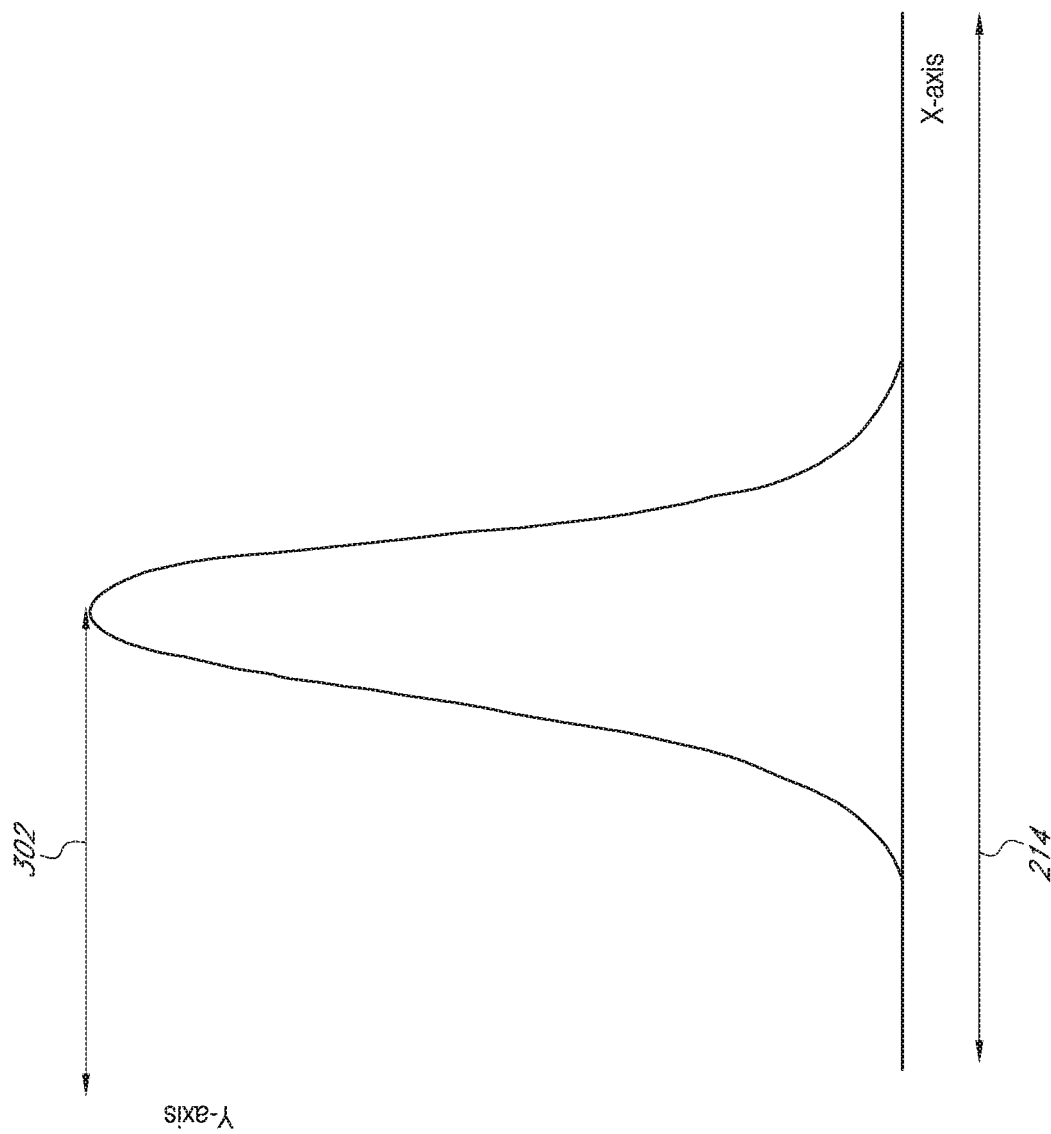
FIG. 3 is an illustration of one example of some of the types of data that can be collected by a flow cytometer.

Referring to FIG. 3, a histogram can be observed that includes several signal plots 206 compiled into a single plot. Each signal plot 206 counts as a single event or can represent a particle 106 passing through the flow cell 116 and producing a signal from one of the channels 120. The y-axis represents the count or number of events and the x-axis represents peak time 216 or data intensity peak time. The apex of the peak is the point in time where the most events occur. In FIG. 3 events are normally distributed. In FIG. 3, peak times 216 added together can be called compiled peak times 302. In flow cytometry, there is always some variance or jitter in particle arrival time which results in events occurring with different peak times 216. In the foregoing specification, the ability to detect accurate peak times 216 is very important. In order to reach statistical significance sometimes 500 events or more need to be averaged. In some situations, 1000 or more events are desired to reach statistical significance and properly assess the compiled peak time 302. Any statistical means can be used that relates to average, median, integration, or slope derivative. Those skilled in the art will appreciate many other ways to analyze variance.

Figure 4A:
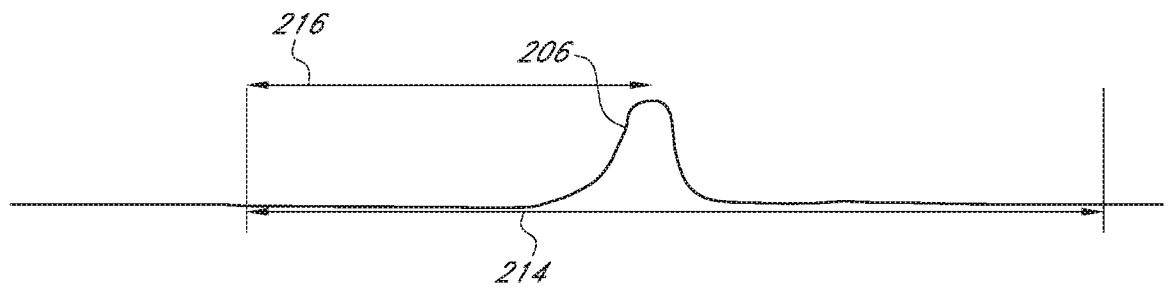
FIGS. 4A and 4B illustrate wide and a narrow data time collection windows.
Figure 4B:
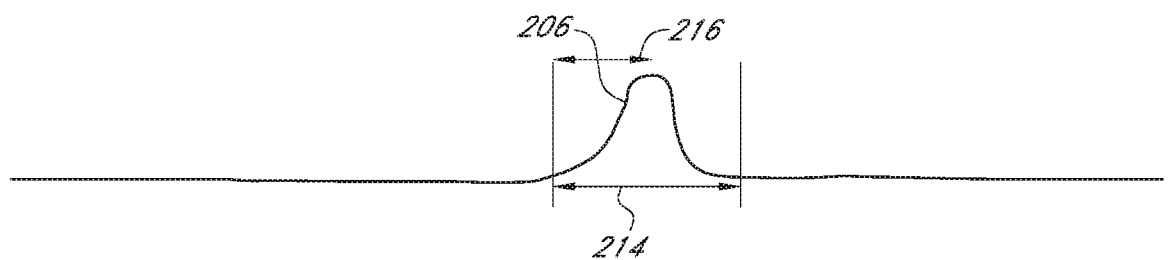

Referring to FIGS. 4A and 4B, two signal plots 206 are depicted. FIG. 4A depicts a wide data collection time window plot 206 and FIG. 4B depicts a narrow data collection time window plot 206. These figures represent an important step in a system or method to determine data processing settings for a flow cytometer. When taking an initial measurement of peak time 216 within a data collection time window 214 there is uncertainty in where the highest peak 204 will occur. Widening the data collection time windows 214 for each of the channels 120 greatly improves the likelihood of discovering the peak 204. As previously mentioned, several data points need to be collected to ensure an accurate representation of compiled peak time 302. Once the compiled peak time 302 is accurately measured the data collection time window 214 can be narrowed as seen in FIG. 4B in order to decrease the likelihood of coincidence and increase the signal to noise ratio. Such a data collection time window 214 size reduction can occur in each channel 120. Data time collection time windows 214 can also be shifted in time.

Figure 5:
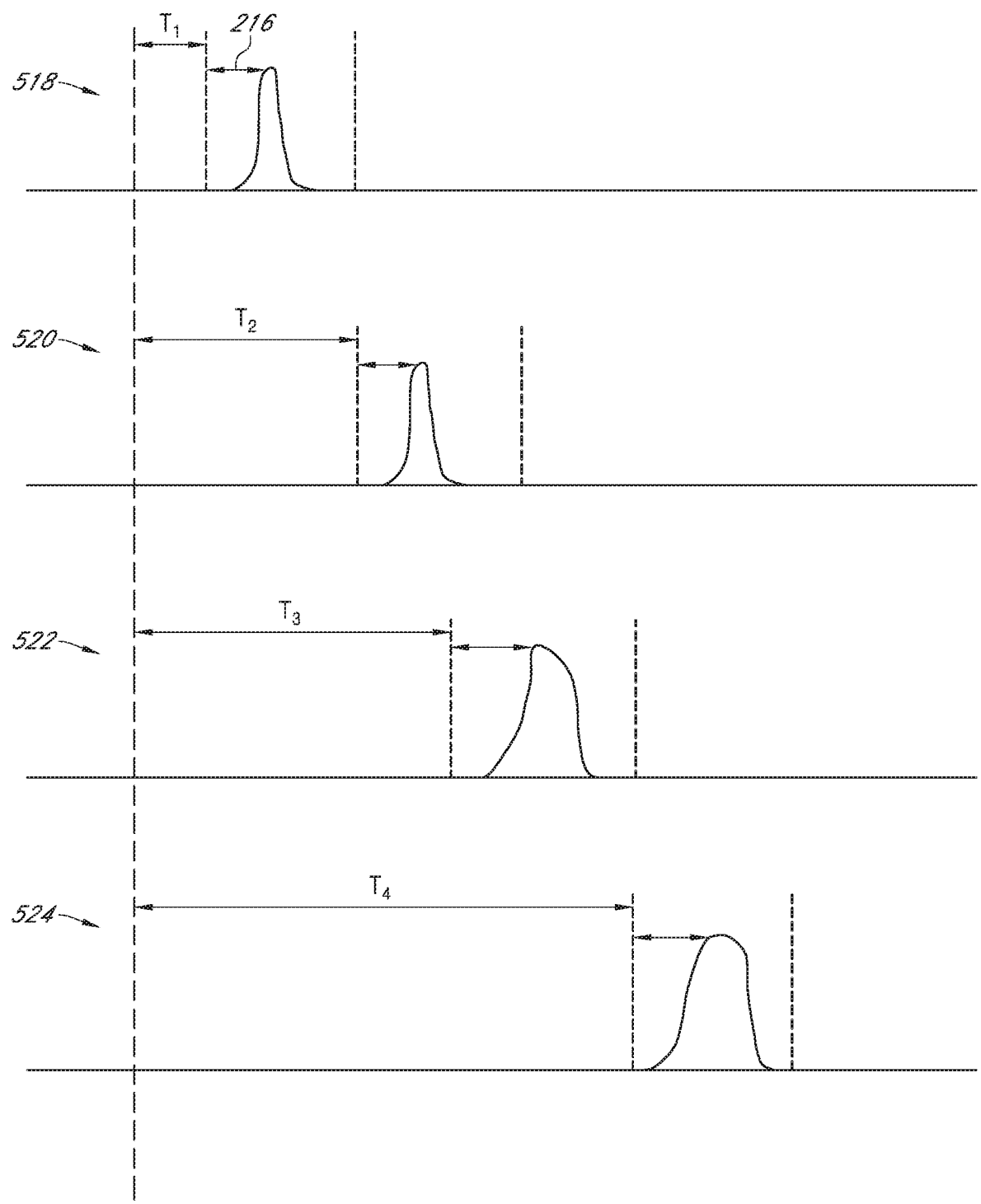
FIG. 5 is an illustration of one example of data coming from four channels in a flow cytometer.

Referring to FIG. 5, four signal plots 206 are illustrated. Each signal plot 206 in FIG. 5 represents a typical signal plot 206 with a typical peak time 216 for the system. Here, the y-axis can be intensity (voltage, fluorescence, brightness, etc.) and the x-axis can be time (This is sometimes referred to in the art as ADC points, relating to an analog to digital converter.). The signal plots 216 represent the same particle passing through four spatially separated channels 518, 520, 522, and 524. In this example, the first channel 518 represents a trigger channel 518. When the trigger threshold 208 is met in the trigger channel 518 the digital sampling electronics 112 begin signal processing for all of the channels 518, 520, 522, and 524.

Before making a time delay determinations using peak time 216 or compiled peak time 302 an approximation can be used based on system settings. These settings can include flow rate through the flow cell or sheath fluid flow rate. Additionally, hardware parameters such as the distance between adjacent light beams 104 pass through a flow cell 116.

When determining the data collection settings the data collection time windows 214 remain wide as seen in FIG. 4A for each of the four spatially separated channels 518, 520, 522, and 524. A time delay derived from the peak time 216 can be set for each of the four spatially separated channels 518, 520, 522, and 524 wherein the time delay is given by the following relationship between data collection time window position $T_i$ and peak time 216.

$$\text{time delay} = T_i + (\overline{\text{peaktime}_i} - \overline{\text{peaktime}_1})$$

where i corresponds to the $i^{th}$ laser position and i=1 is the trigger channel 216. It is common to set $T_1=0$. Note that the trigger channel can be any channel and the time delay can be positive or negative.

Channels further away from the trigger channel 518 in space will have the longest time delays. Once an accurate measurement of the peak times 216 for all the channels 518, 520, 522, and 524 has been measured by the digital sampling electronics 112 the time delays can be adjusted for each of the channels 518, 520, 522, and 524 and the time collection data windows 214 can be narrowed to optimize the signal to noise ratio and reduce coincidence. Generally, the highest peak 204 average will be centered within the time collection data windows 214 for each channel 518, 520, 522, and 524. However, centering is not required and in some circumstances may not be optimal. It should be noted that such a procedure can be used for two or more channels and that FIG. 5 is only one example of several embodiments.

In various embodiments, the initial wide time collection data windows 214 can range from about 320 to 360 ADC points. and the narrowed time collection data windows 214 can range from about 80 to about 120 ADC points. In various embodiments, the extensions can be about 27 ADC points for the narrowed windows. In various embodiments, the extensions can range from about 17 to about 37 ADC points.

Figure 6:
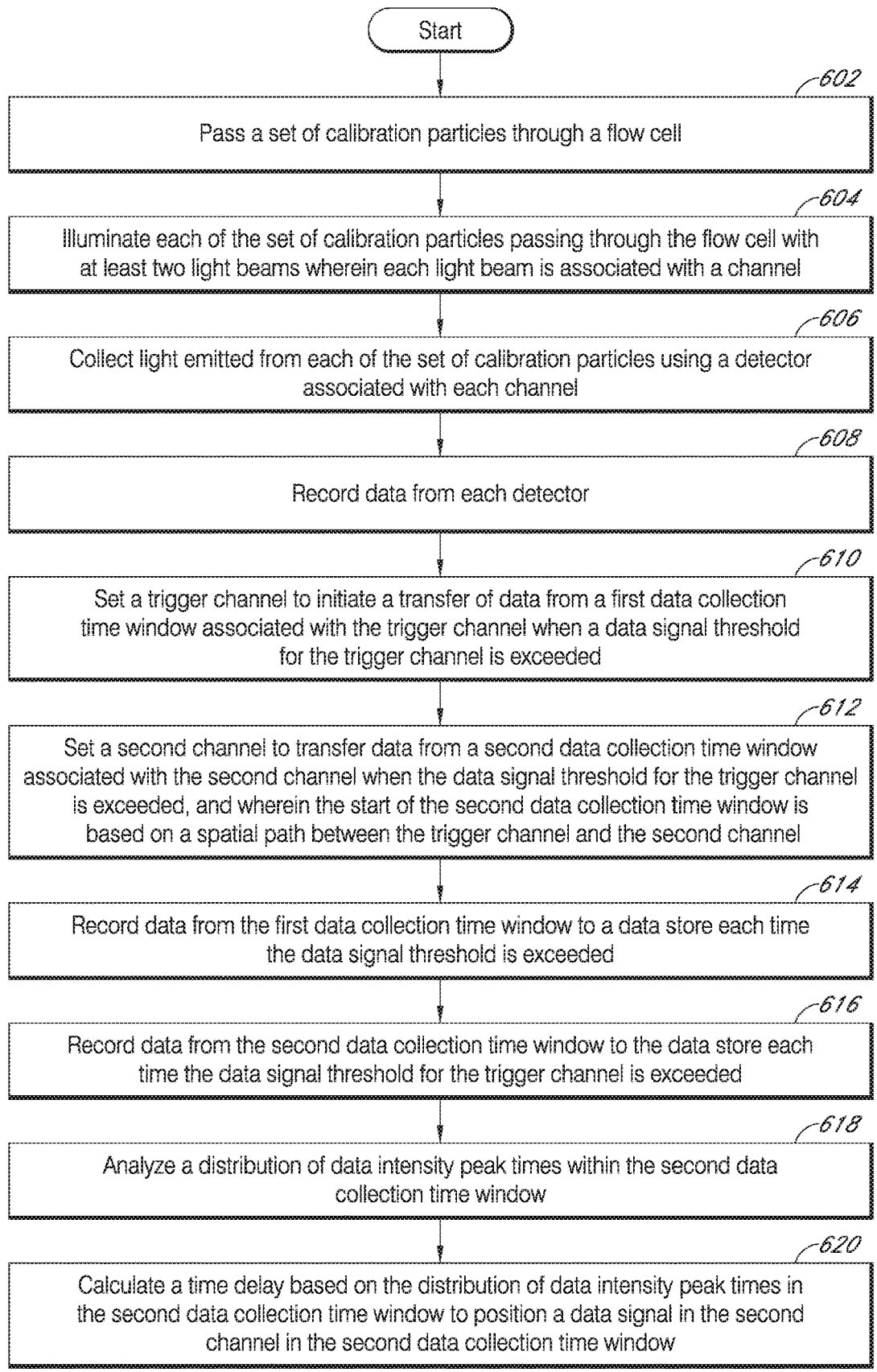
FIG. 6 is an example embodiment of a method for determining data processing settings for a flow cytometer.

FIG. 6 illustrates one example of various embodiments of a method to determine data processing settings for a flow cytometer comprising passing a set of calibration particles through a flow cell 602. Various embodiments can include illuminating each of the set of calibration particles passing through the flow cell with at least two light beams wherein each light beam is associated with a channel 604. Various embodiments can include collecting light emitted from each of the set of calibration particles using a detector associated with each channel 606. Various embodiments can include recording data from each detector 608. Various embodiments can include setting a trigger channel to initiate a transfer of data from a first data collection time window associated with the trigger channel when a data signal threshold for the trigger channel is exceeded 610. Various embodiments can include setting a second channel to transfer data from a second data collection time window associated with the second channel when the data signal threshold for the trigger channel is exceeded, and wherein the start of the second data collection time window is based on a spatial path between the trigger channel and the second channel 612. Various embodiments can include recording data from the first data collection time window to a data store each time the data signal threshold is exceeded 614. Various embodiments can include recording data from the second data collection time window to the data store each time the data signal threshold for the trigger channel is exceeded 616. Various embodiments can include analyzing a distribution of data intensity peak times within the second data collection time window 618. Various embodiments can include calculating a time delay based on the distribution of data intensity peak times in the second data collection time window to position a data signal in the second channel in the second data collection time window 620.

Figure 7:
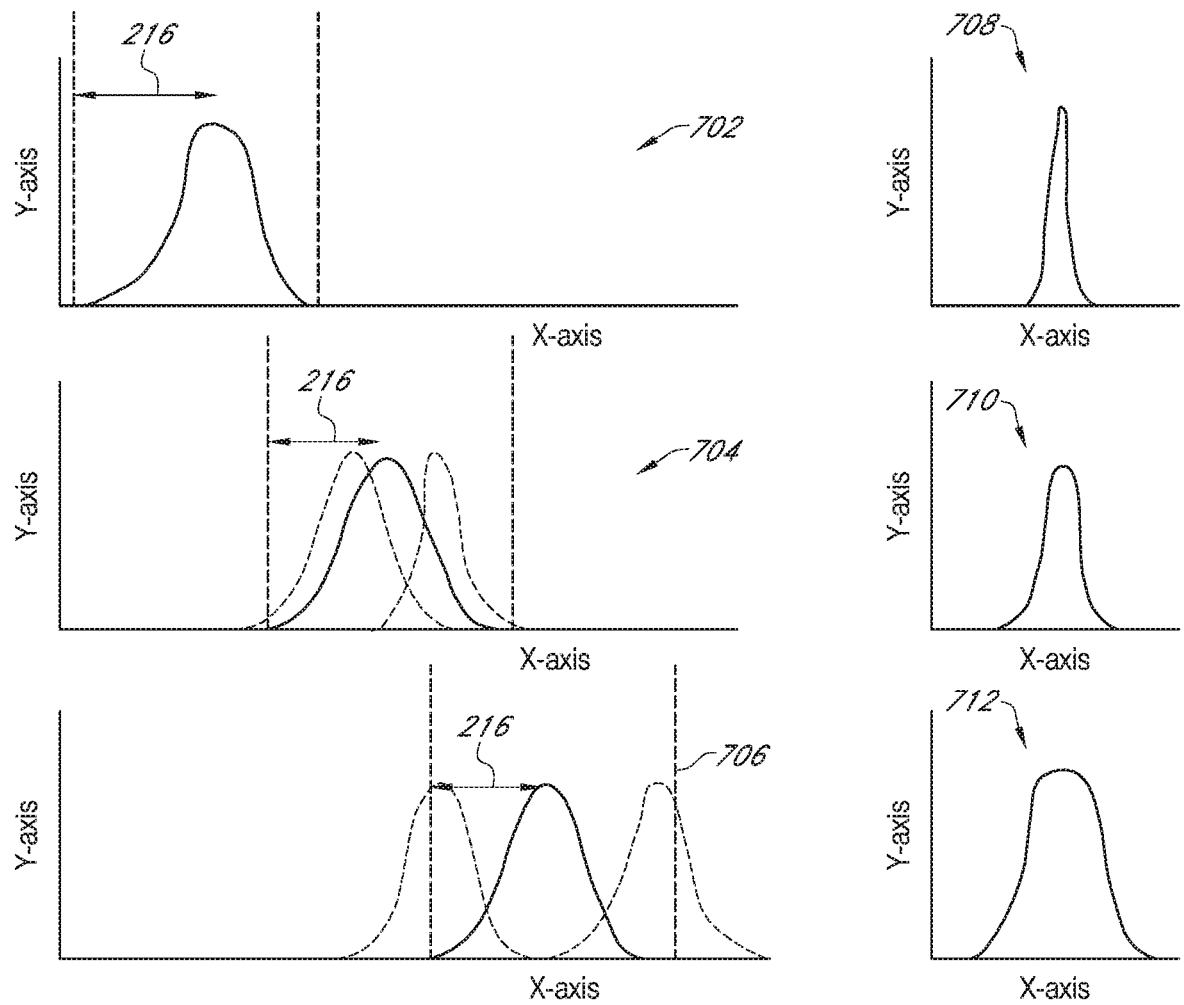
FIG. 7 is an illustration of one example of data from a flow cytometer where peak time spread increases as a function of distance from the trigger channel.

Referring to FIG. 7, three data collection plots 702, 704, and 706 are illustrated with each having an accompanying compiled data plot (or histogram) 708, 710, and 712. For the data collection plots 702, 704, and 706, the x-axis can represent time and the y-axis represents signal intensity. The first data collection plot 702 represents the trigger channel 702 where there is little to no peak time 216 fluctuation. The adjacent data collection plot 704 depicts three curves. The dotted curves symbolize fluctuation in particle arrival time. The furthest channel 120 or data collection plot 706 from the trigger channel 702 has the most peak time 216 fluctuation because fluctuations can compound over longer distances.

When diagnosing whether there is a fluidic failure peak time 216 arrival can provide important evidence. For example, the data collection plot 706 for the furthest channel from the trigger channel has curves that fall outside of the optimized data collection time window 214. Such data 114 can be processed sub-optimally or simply never be processed and can lead to missing data and to inferior results. In certain situations the data collection time windows 214 can be opened to collect more data 114, but coincidence will increase as well as noise.

The compiled data plots 708, 710, and 712 show a histogram comprising events or count on the y-axis and peak time 216 on the x-axis taken from many particle measurements of peak time 216 on the system. The compiled data 708 for the trigger channel illustrates a tight data distribution where most of the events or particles passing through the channel occur within a small time range. It is expected that the spread will become wider as the particle travels a longer distance which can be seen in the other compiled data plots 710 and 712.

Figure 8A:
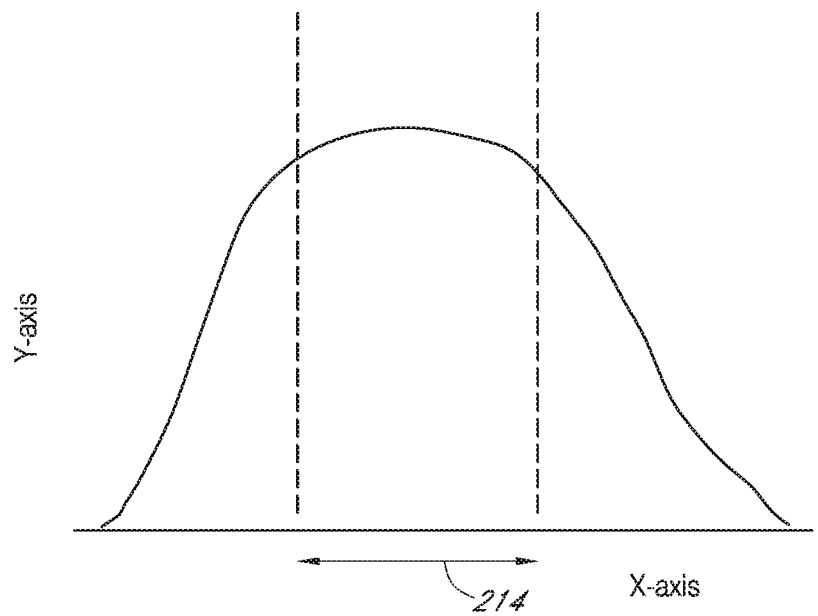
FIG. 8A illustrates peak times outside a system specification.
Figure 8B:
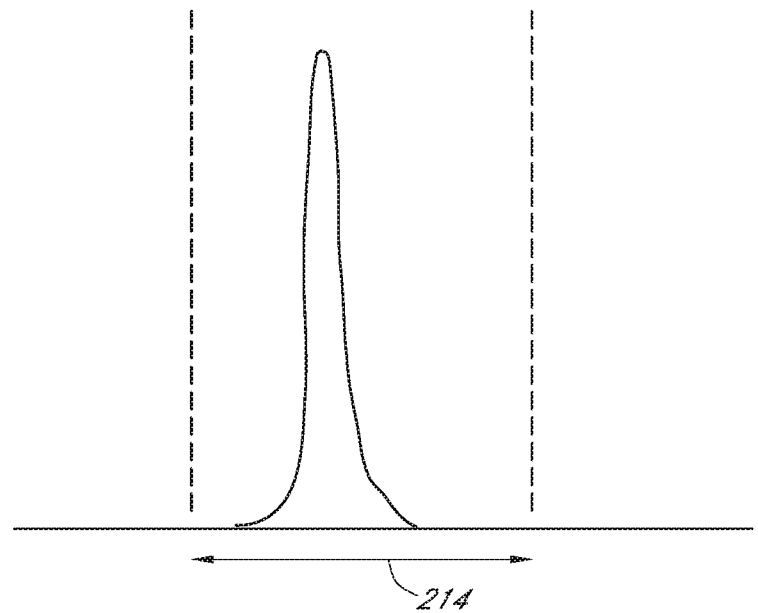
FIG. 8B illustrates peak times within a system specification.

Referring to 8A an example of a histogram of peak time values 216 showing low quality compiled data where most of the data 114 does not fall within the data collection time window 214 as a result of fluidic fluctuations in system. The data falls outside a predetermined system specification shown by the dashed lines. FIG. 8B is an example of a histogram of peak time values 216 showing high quality compiled data plot where all of the data 114 falls within the data collection time window 214 as a result of a fluidic system within operating specification. Data 114 such as that found in FIG. 8A can indicate a fluidics instability problem. Note that these drawings are not to scale and the intent for this example is that the data collection time windows 214 are the same width which means that the events in FIG. 8A are spread much further apart than the events in FIG. 8B.

FIG. 9A-E are all examples of the types of data 114*b* generated from the embodiments disclosed herein that would indicate a failure in a fluidics system.

Figure 9A:
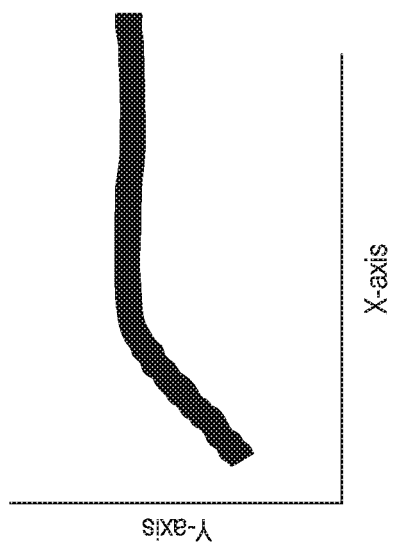
FIG. 9A-E are illustrations of what flow cytometry data can look like when there is a fluidics failure.
Figure 9B:
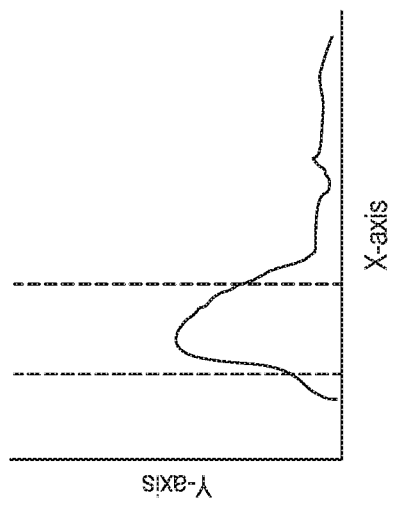

Referring to FIG. 9A, the y-axis represents number of events and the x-axis represents a histogram of peak time 216 (where a highest peak 204 occurs in relation to the data collection time window 214). In FIG. 9A the area in between the dashed lines represents what is acceptable for the system specification for a given experiment. In this example, the distribution of peak times 216 have a high point and a tail to the right. The tail indicates that a lot of fluidic fluctuation and/or pulsation occurred during this run. FIG. 9B is the same run as 9A and shows fluorescence on the y-axis and time on the x-axis. As time progresses, fluorescence or signal intensity increases. Both 9A and 9B taken together indicate that a problem in the fluidics system occurred early in an experiment or run and self-corrected. A trapped air bubble in the system can cause such a result. Generally, any distribution that is not normal indicates some kind of fluidics problem or failure.

Figure 9D:
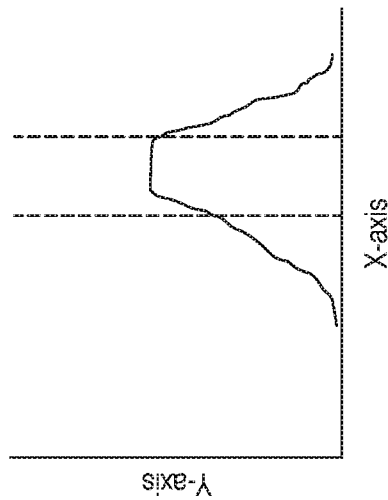
Figure 9C:
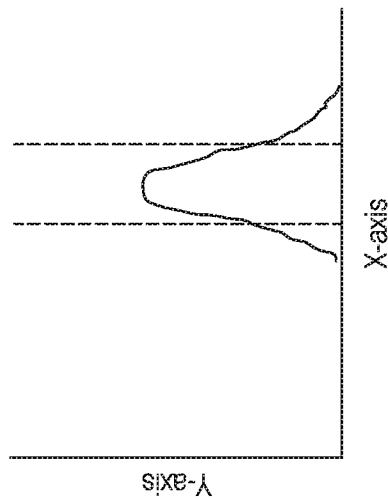

FIG. 9C depicts event count on the y-axis and the fluorescence intensity on the x-axis with a distribution that is too broad to meet specification. Such data 114 can be the result of light source 102 misalignment, collection optics issues, excessive noise on the collection electronics, or a variety of compounding issues. See the referenced literature above for a more detailed discussion. However, when peak time 216 information is gathered, such as in FIG. 9D (event count on the y-axis, peak time on the x-axis), and analyzed in conjunction with FIG. 9C then a determination can be made that there is likely a fluidics failure. In determining if peak time 216 spread is beyond acceptable limits, monitoring the amount of the data 114 that falls outside of the data collection time window 214 can be important. In various embodiments, that can be ten percent or more. In FIGS. 9C and 9D the area in between the dashed lines represents what is acceptable for the system specification for a given experiment.

Figure 9E:
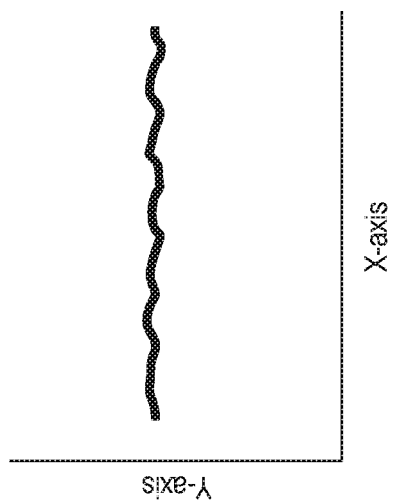
Figure 10:
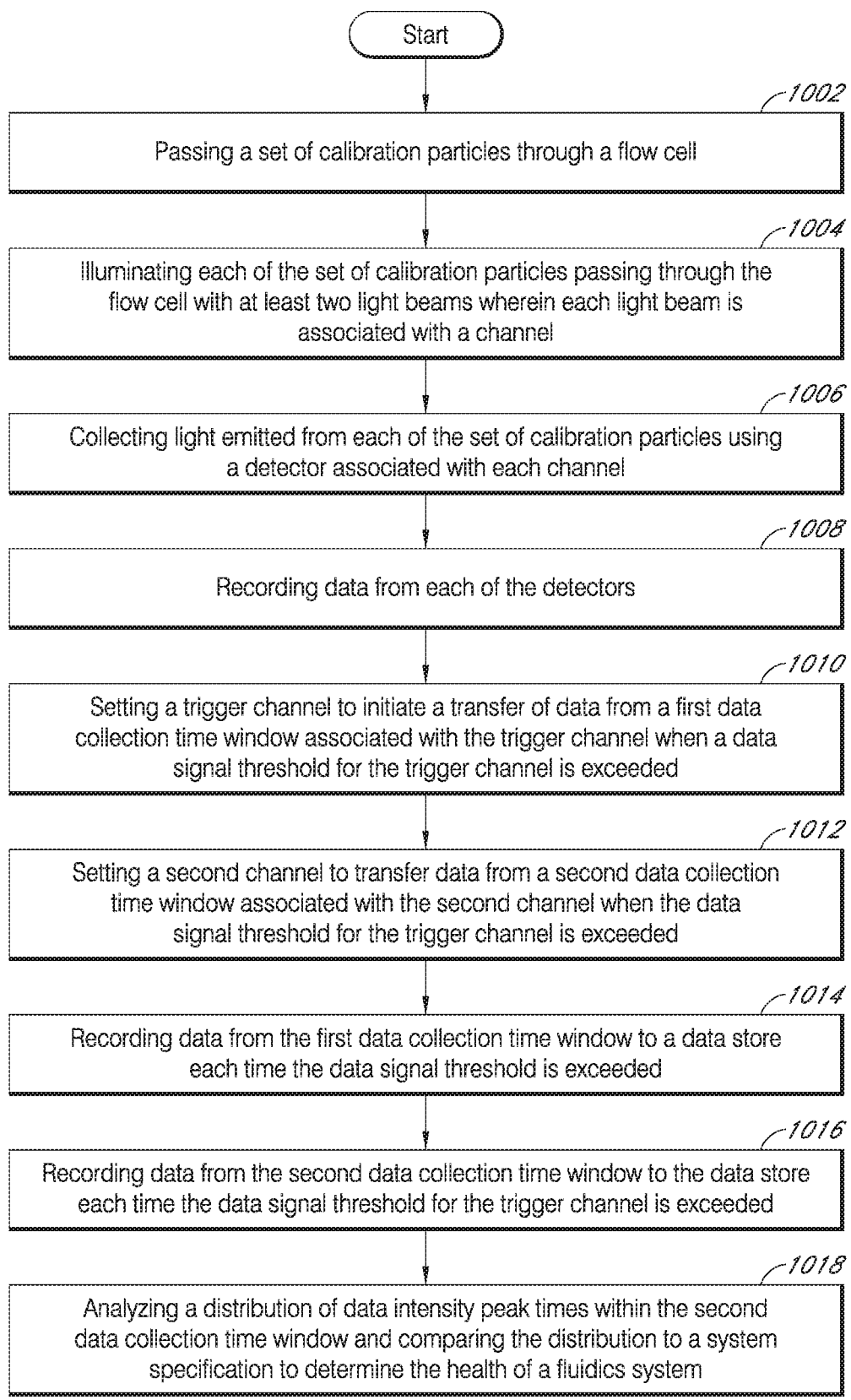
FIG. 10 is an example embodiment of a method to diagnose a fluidics system for a flow cytometer.

FIG. 9E depicts peak time 216 of subsequent particles in a run on the y-axis and time and the x-axis. From this example, it can be inferred that particle 106 arrival is not constant over time and can indicate a serious fluidic failure if the variation in peak time 216 is too large and not with the system specification. The cause of such a failure is often from pulsation from the sheath delivery system. Before the set of current embodiments, a diagnosis for such a problem would have involved a circuitous process involving a lot of time wasted. Using peak time 216 data where the location of the highest peaks 204 are known within a data collection time window 214 such a diagnosis becomes far simpler.

FIG. 6 illustrates one example of various embodiments of a fluidic diagnostic method for a flow cytometer comprising passing a set of calibration particles through a flow cell 1002. Various embodiments can include illuminating each of the set of calibration particles passing through the flow cell with at least two light beams wherein each light beam is associated with a channel 1004. Various embodiments can include collecting light emitted from each of the set of calibration particles using a detector associated with each channel 1006. Various embodiments can include recording data from each of the detectors 1008. Various embodiments can include setting a trigger channel to initiate a transfer of data from a first data collection time window associated with the trigger channel when a data signal threshold for the trigger channel is exceeded 1010. Various embodiments can include setting a second channel to transfer data from a second data collection time window associated with the second channel when the data signal threshold for the trigger channel is exceeded 1012. Various embodiments can include recording data from the first data collection time window to a data store each time the data signal threshold is exceeded 1014. Various embodiments can include recording data from the second data collection time window to the data store each time the data signal threshold for the trigger channel is exceeded. Various embodiments can include analyzing a distribution of data intensity peak times within the second data collection time window and comparing the distribution to a system specification to determine the health of a fluidics system 1016. Various embodiments can include the system specification being 1 standard deviation. Various embodiments can include the system specification being 2 standard deviation. Various embodiments can include the system specification being 3 standard deviation. Various embodiments can include the system specification being 4 standard deviation. Various embodiments can include the system specification being a Gaussian distribution. Various embodiments can include the system specification being a Poisson distribution. Various embodiments can include the system specification being any statistical distribution. Various embodiments can include the light emitted being fluorescent. Various embodiments can include the light emitted being scattered. Various embodiments can include the data collection time windows being between about 80 to about 120 ADC points wide. Various embodiments can include the data collection time windows being between about 320 to about 360 ADC points wide.

In various embodiments, the method can include the step of impacting the particles 106 with the light beams 104 to produce data from each of the spatially separated channels 120.

In various embodiments, the method can include the step of detecting a signal from the particles 106 using a detector 110.

In various embodiments, the data 114 can include peak time 216. In various embodiments, the data 114 can include height, width, and area data.

In various embodiments, the peak time 216 data can be used in the step of evaluating the data.

In various embodiments, evaluating the data 114 can include determining if greater than ten percent of the peak time 216 data falls outside of the data collection time window 214.

In various embodiments, evaluating the data 114 can occur using a digital sampling electronics 112.

In various embodiments, the data collection time windows 214 can be about three point five microseconds.

In various embodiments of the fluidic diagnostic method and method for determining data processing for a flow cytometer, the light beam 104 can have a larger diameter than each of the particles 106. Such a configuration allows for signal intensities to be calculated without the need for integration. In other words, height and area, which are described elsewhere in the literature, can be proportionate. However, alternatively integration can be used which becomes especially useful when particle 106 diameter exceeds light beam 104 diameter.

EXAMPLE 1

High Quality Fluorescence and Peak Time Data

Figure 11B:
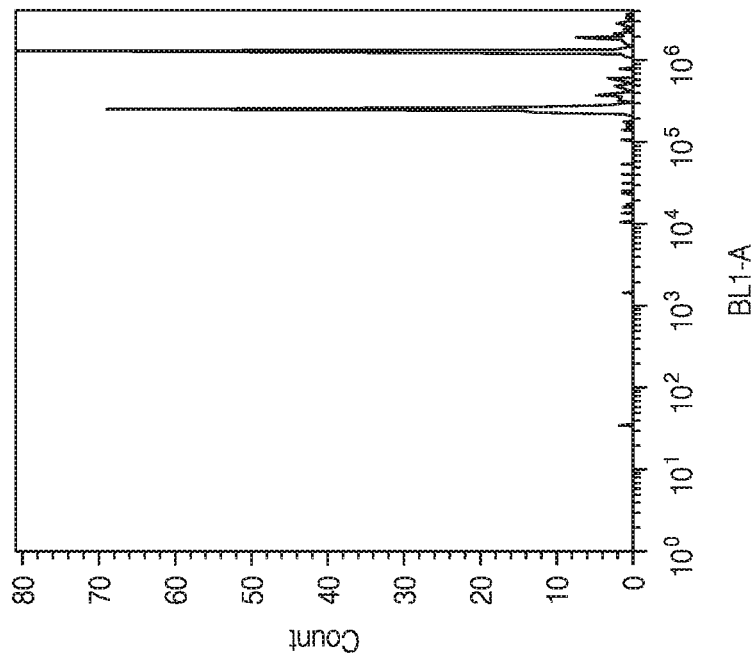
FIGS. 11A-11L illustrate data from a flow cytometer representative of a healthy fluidics system.
Figure 11A:
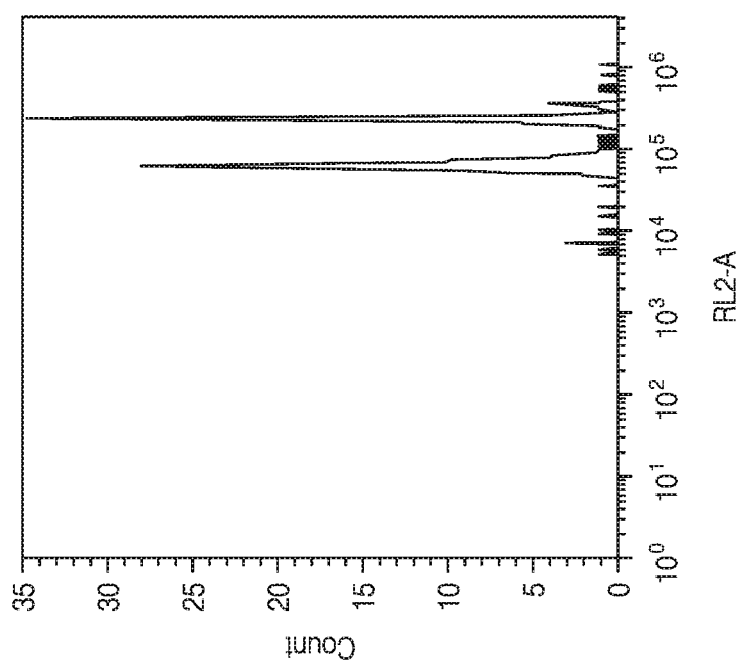
Figure 11D:
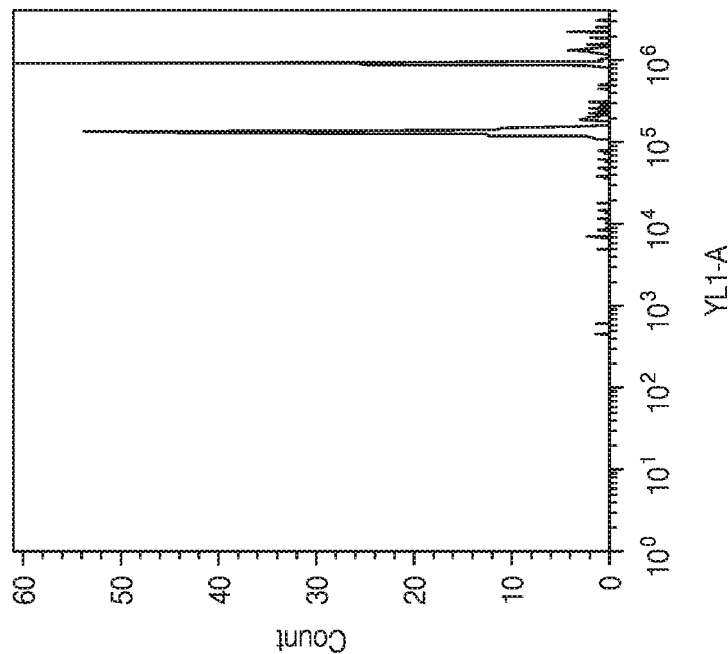
Figure 11C:
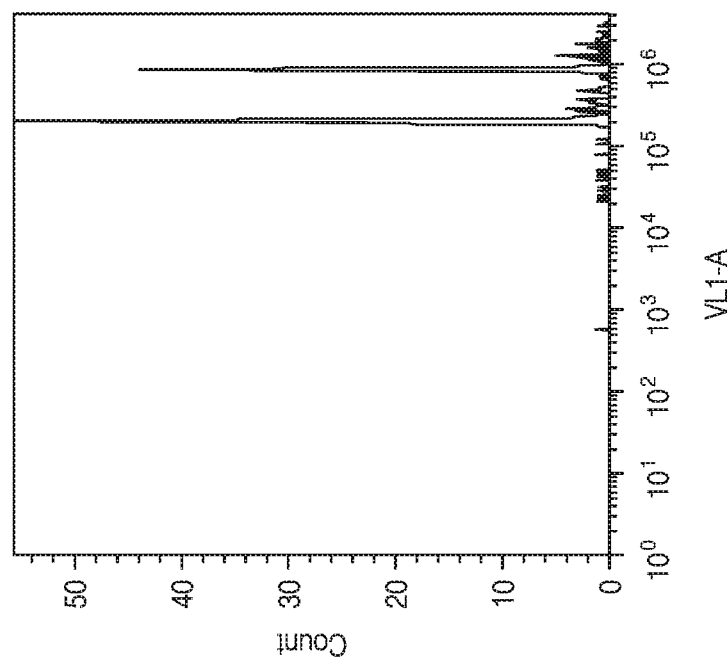
Figure 11F:
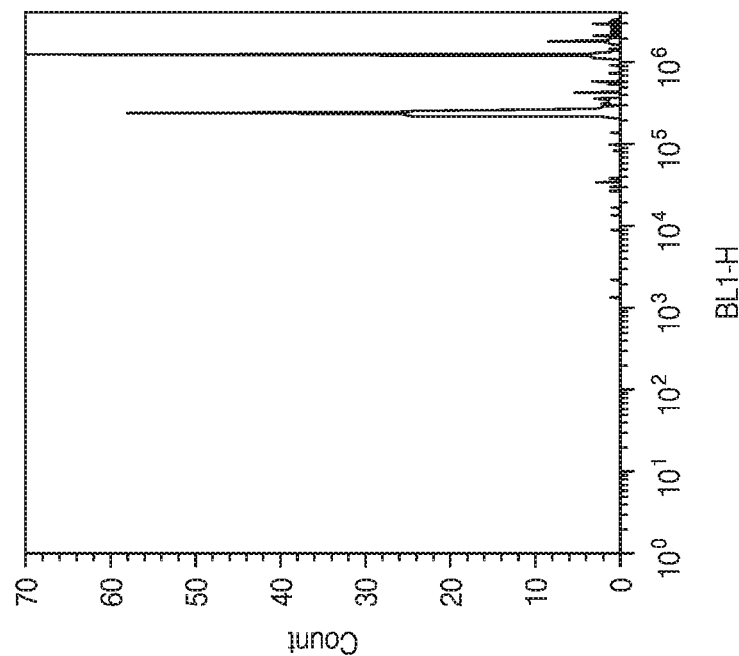
Figure 11E:
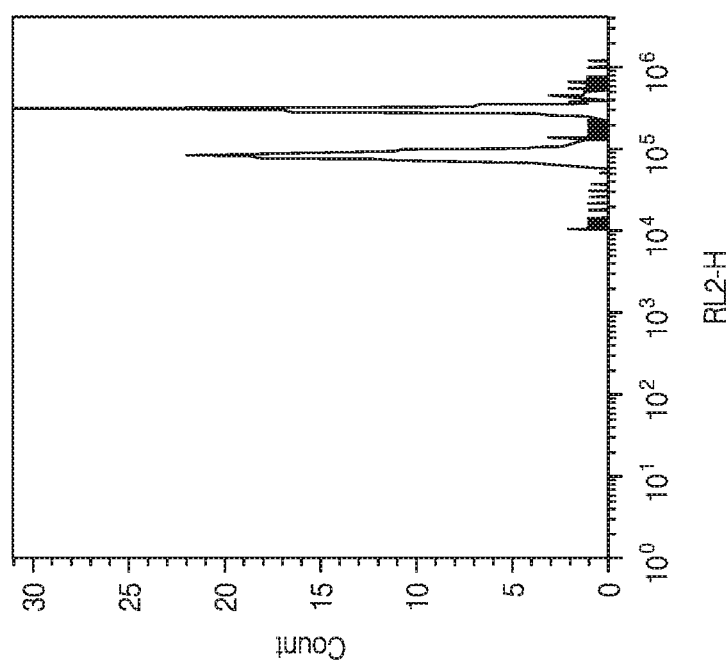
Figure 11H:
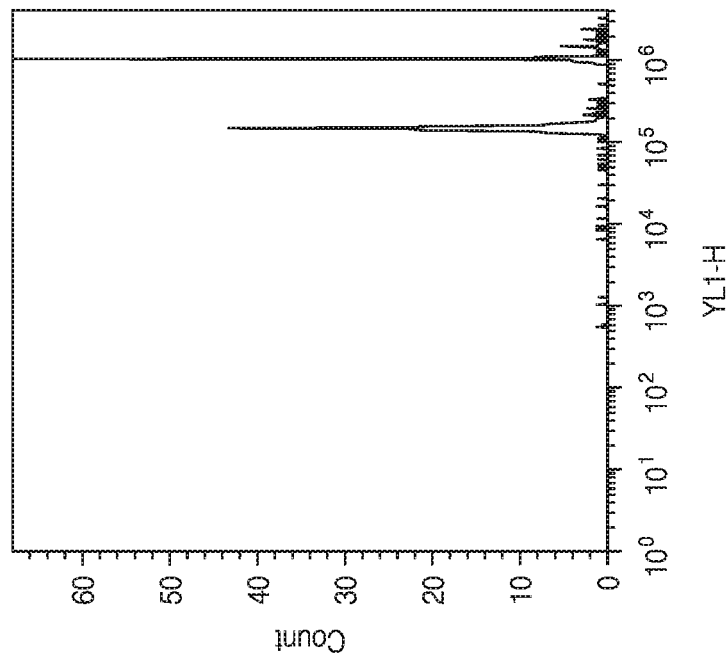
Figure 11G:
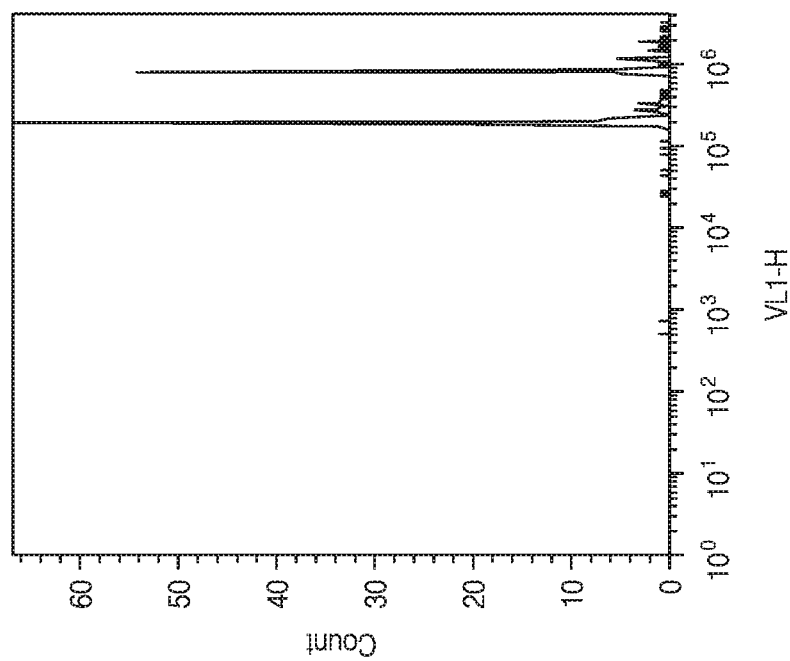
Figure 11J:
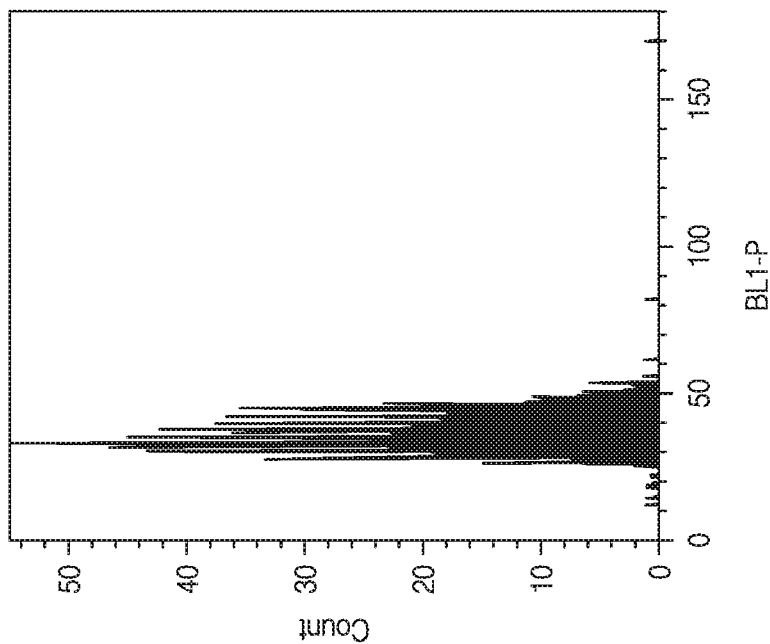
Figure 11I:
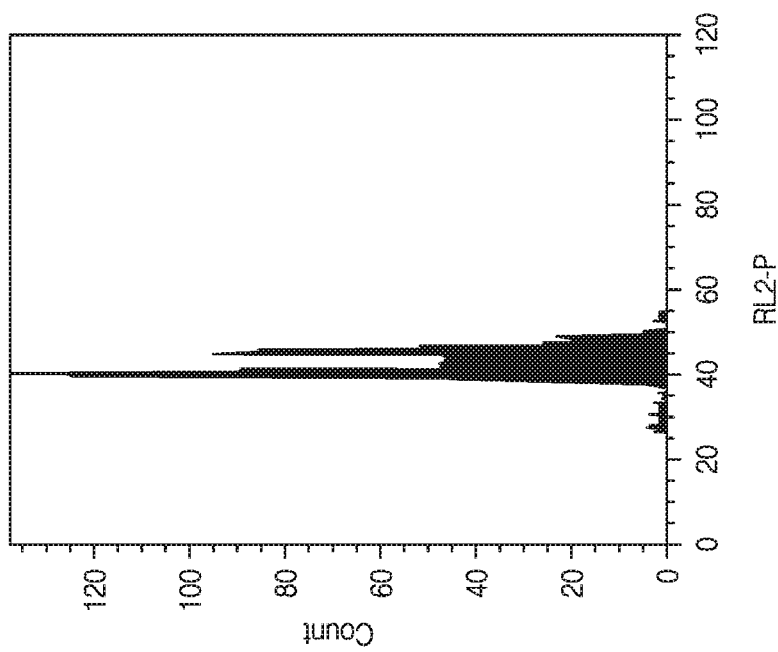
Figure 11L:
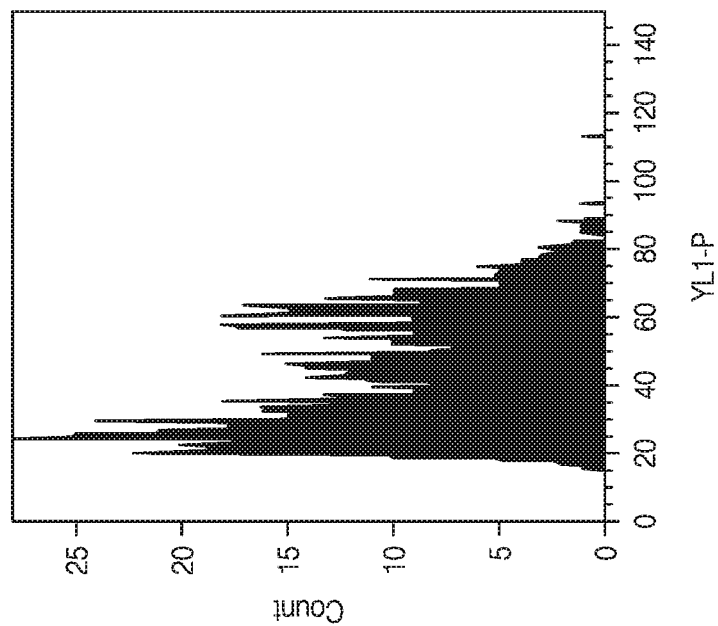
Figure 11K:
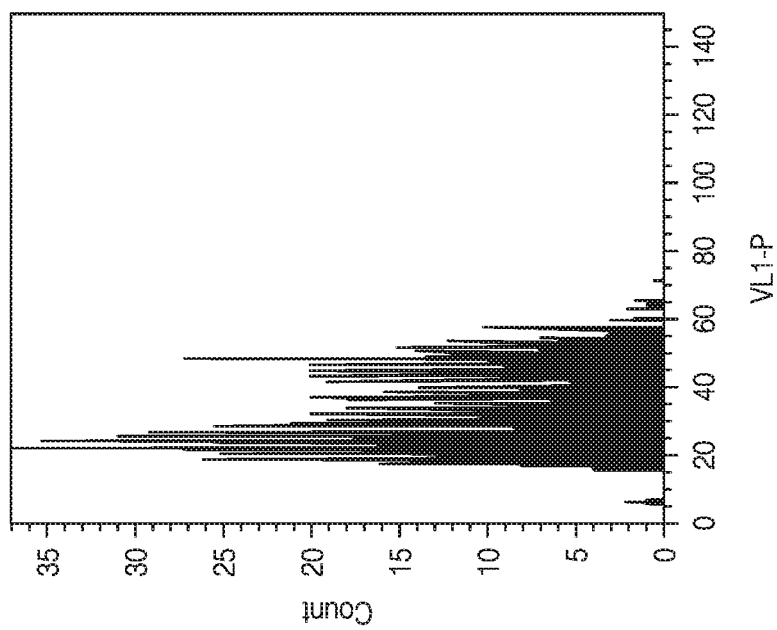

Fluorescence and peak time 216 data 114 were gathered for four channels 120 in a flow cytometer. FIGS. 11A, 11E, and 11I depict data from a red light source 102. FIGS. 11B, 11F, and 11J depict data from a blue light source 102. FIGS. 11C, 11G, and 11K depict data from a violet light source. FIGS. 11D, 11H, and 11L depict data from a yellow light source. FIGS. 11A-11H show count or events on the y-axis and fluorescence intensity on the x-axis. The plots in FIG. 11 depicted with an "A" in the channel name are histograms of signal area measurements and the plots depicted with an "H" in the measurement are histograms of signal height measurements. In the example seen in FIG. 11, beads with two different fluorescent intensities were used which is why there are two peaks. FIGS. 11I-11L depict count or events on the y-axis and peak time on the x-axis (measured in ADC points).

In FIGS. 11A-11H two crisp peaks are visible in each plot, indicating strong signal intensity.

In FIGS. 11I-11L, histograms of peak time 216 are shown from the particle data that generated the data shown in FIGS. 11A-11H (11A and 11E correspond to 11I, 11B and 11F correspond to 11J, 11C and 11G correspond to 11K, and 11D and 11H correspond to 11L). FIG. 11I shows the tightest peak because it is the trigger channel. As each channel 120 gets further away from the trigger channel the plot becomes wider (compare FIGS. 11I, 11J, 11K, and 11L). However, the spread is still within specification and fits into a data collection time window 214 that is 120 ADC points wide.

Overall, this example demonstrates a healthy fluidics system.

EXAMPLE 2

Low Quality Fluorescence and Peak Time Data

Figure 12B:
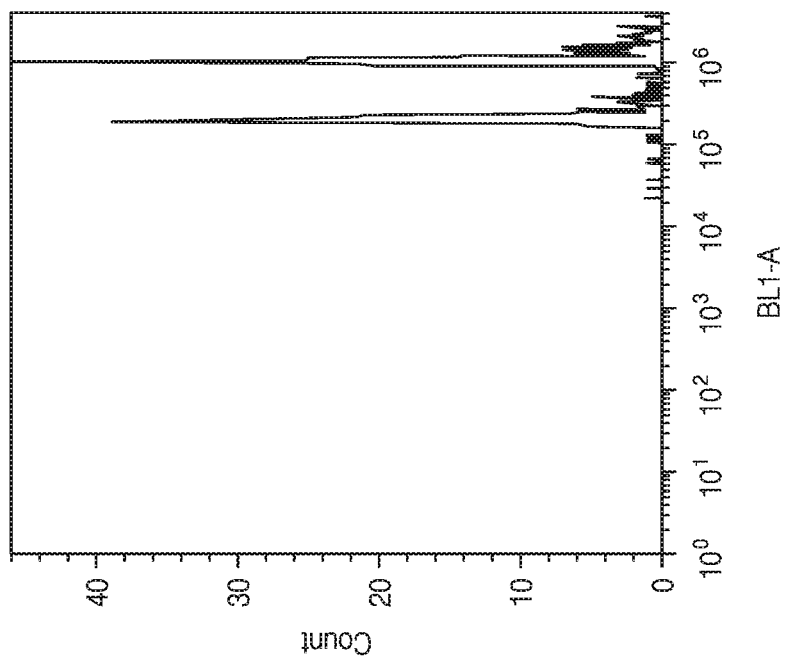
FIGS. 12A-12L illustrate data from a flow cytometer representative of a fluidics system failure.
Figure 12A:
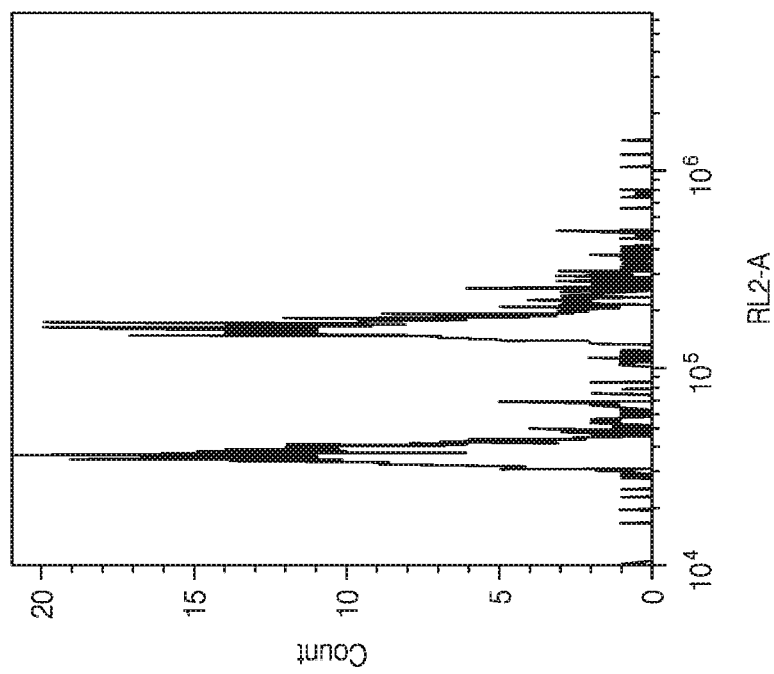
Figure 12D:
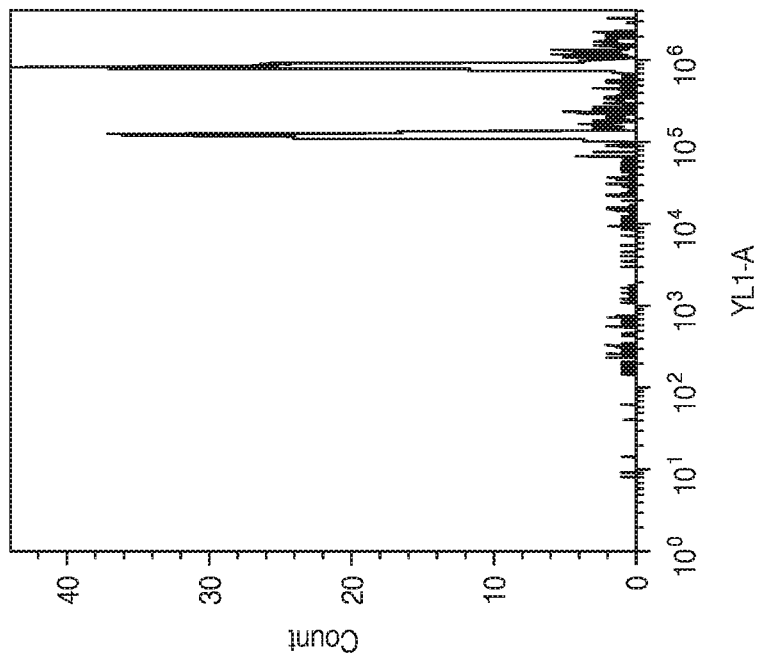
Figure 12C:
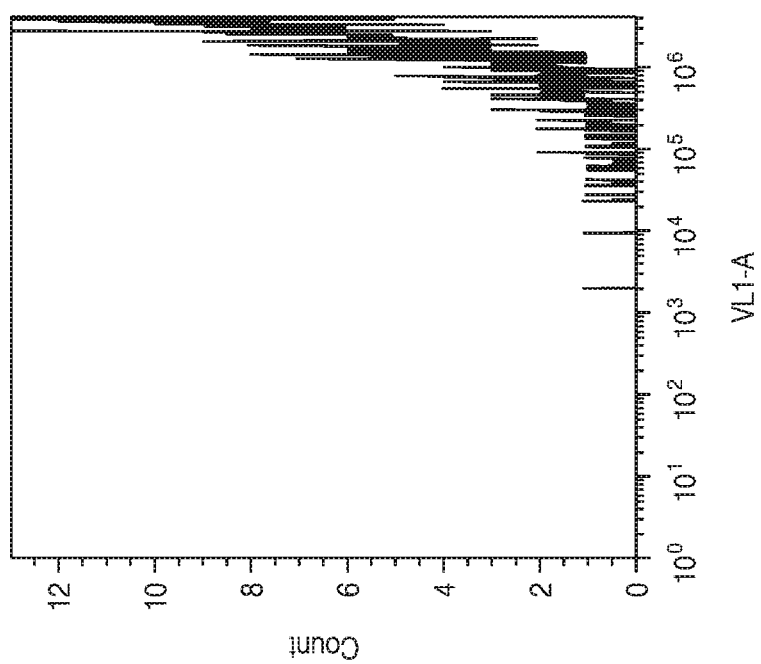
Figure 12F:
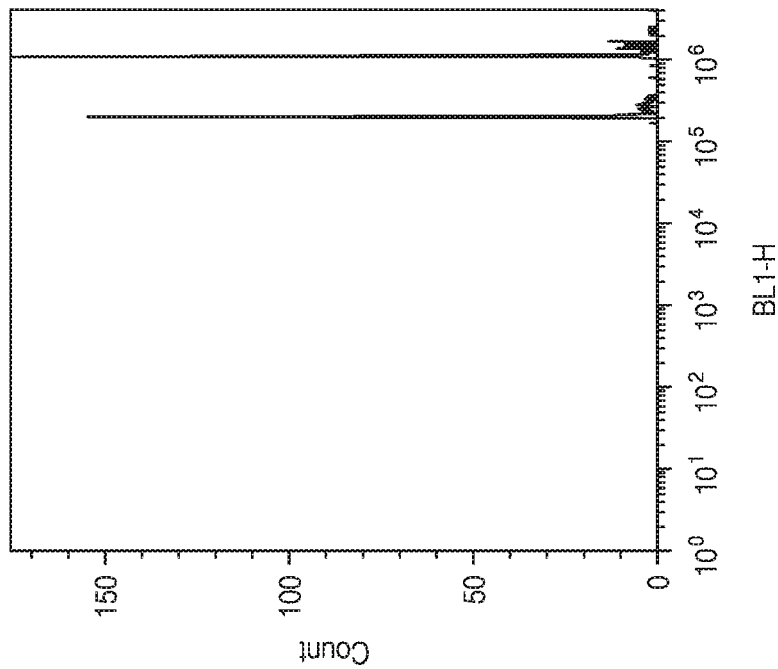
Figure 12E:
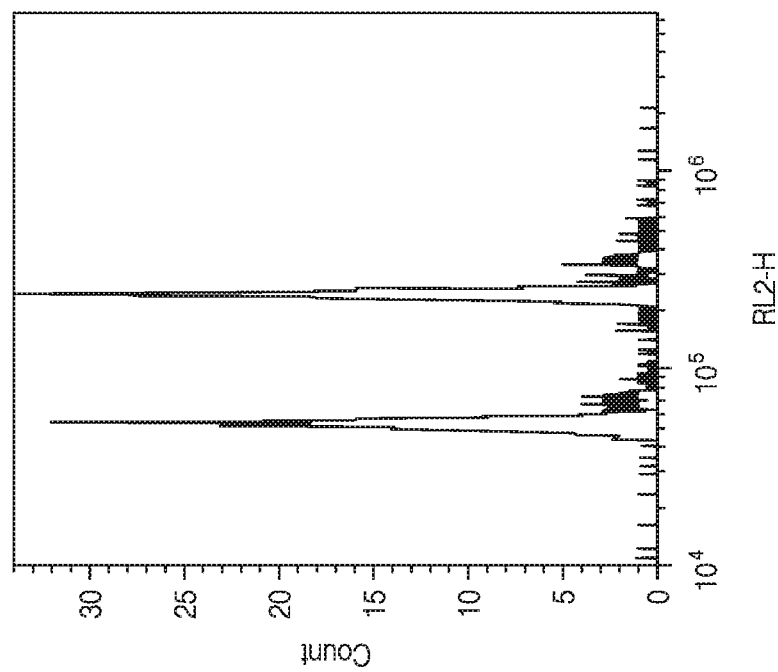
Figure 12H:
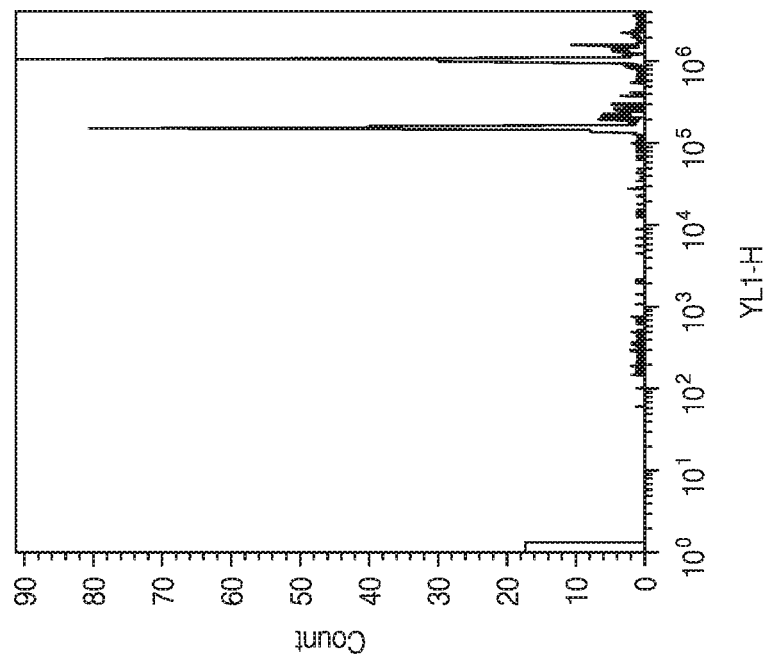
Figure 12G:
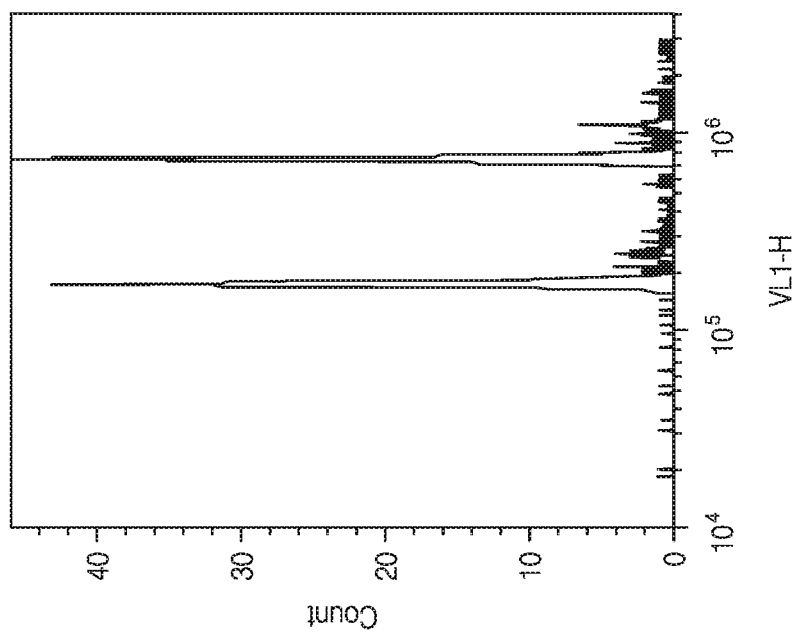
Figure 12J:
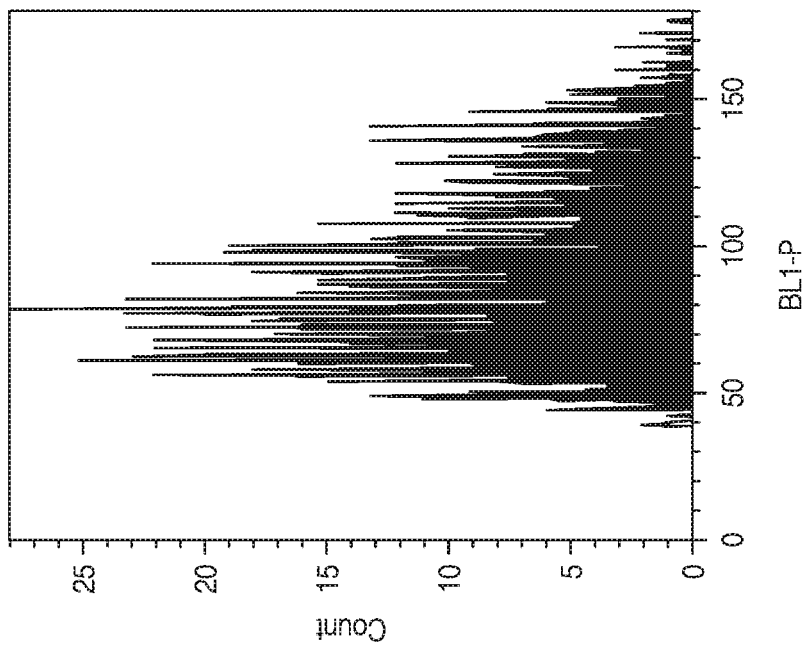
Figure 12I:
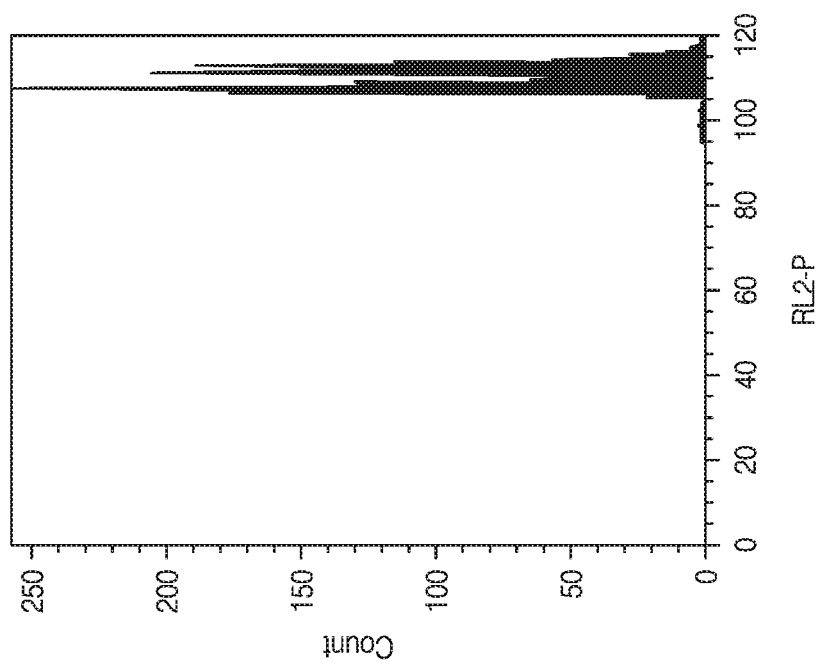
Figure 12L:
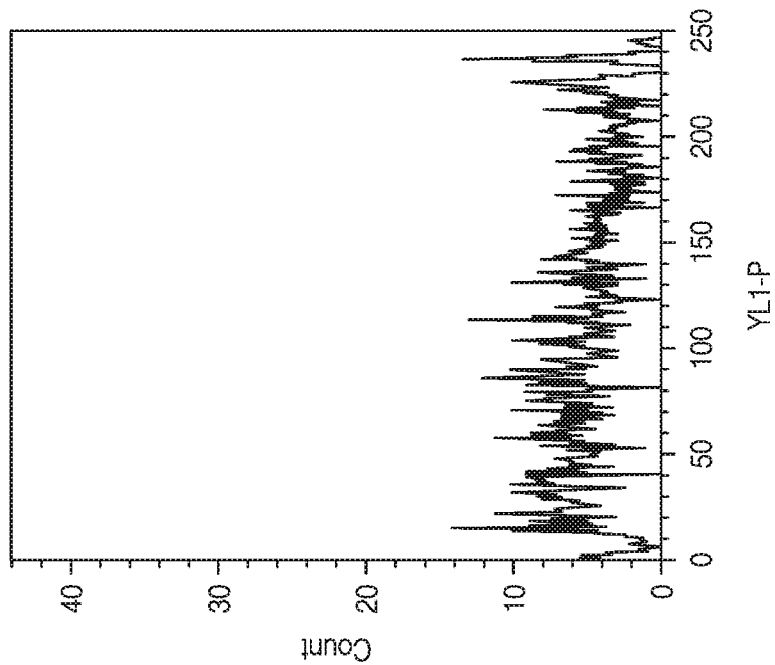
Figure 12K:
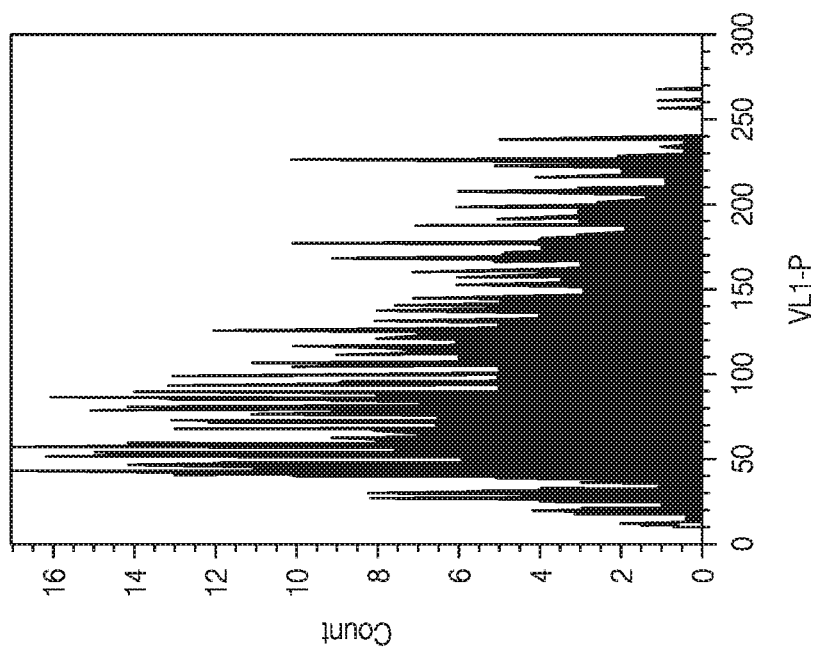

Fluorescence and peak time 216 data 114 were gathered for four channels in a flow cytometer. FIGS. 12A, 12E, and 12I depict data from a red light source 102. FIGS. 12B, 12F, and 12J depict data from a blue light source 102. FIGS. 12C, 12G, and 12K depict data from a violet light source. FIGS. 12D, 12H, and 12L depict data from a yellow light source. FIGS. 12A-12H show count or events on the y-axis and fluorescence intensity on the x-axis. In this example, two fluorophores were used which is why there are two peaks. FIGS. 11I-11L depict count or events on the y-axis and peak time on the x-axis (measured in ADC points).

In FIGS. 12A-12H two peaks are visible in most of the plots, but there is a lot of visible noise along the x-axis. Such a result would indicate the flow cytometer is malfunctioning in some way, but the type of malfunction may not be apparent.

In FIGS. 12I-12L, FIG. 12I shows a tight peak, but the other plots, FIGS. 12J-12L degrade rapidly with the plot in 12L only showing noise along the x-axis despite the data collection time window 214 being widened to 350 ADC points. This data indicates that there is extreme fluidics fluctuation within the system because particles are arriving at the last channel almost randomly (a flat distribution) when they should be arriving fairly close in time. There is a fluidics failure of some kind and possibly a sheath fluid pump failure.

The current system and method for diagnosing a fluidics system for a flow cytometer can accommodate particles 106 flowing at a rate of up to 35,000 particles 106 per second and can be ten times faster than the conventional means of diagnosing. This rate can be higher with the use of faster ADC's, faster digital processors, and higher fluid velocities.

While the present teachings are described in conjunction with various embodiments, it is not intended that the present teachings be limited to such embodiments. On the contrary, the present teachings encompass various alternatives, modifications, and equivalents, as will be appreciated by those of skill in the art. The detection modalities as described herein refer to flow cytometry as the aforementioned particle detection platform. This is also applicable to fluid and/or air stream particle detection beyond the constructs of optical resolving methods and/or flow cytometry and can be used as a particle stream fluctuation measurement method for any general particle stream. Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A fluidic diagnostic system for a flow cytometer comprising:
   a flow cell configured to flow calibration particles;

at least two light sources each configured to emit a light beam, wherein each light beam is associated with a channel, and wherein the light beams pass through the flow cell;

a detector associated with each channel, wherein each detector is configured to collect light emitted from each of the set of calibration beads;

a memory buffer configured to record data from each of the detectors;

a trigger channel configured to initiate a transfer of data from a first data collection time window associated with the trigger channel when a data signal threshold for the trigger channel is exceeded;

a second channel configured to transfer data from a second data collection time window associated with the second channel when the data signal threshold for the trigger channel is exceeded;

a trigger processor configured to:
  transfer the data from the first data collection time window to a data storage each time the data signal intensity threshold is exceeded; and
  transfer the data from the second data collection time window to the data storage each time the data signal intensity threshold is exceeded; and a computer processor configured to compare a distribution of data intensity peak times within the second data collection time window to a system specification to determine a diagnostic parameter.

2. The system in claim 1, further comprising a field programmable gate array wherein the memory buffer and the trigger processor are subcomponents of the field programmable gate array.

3. The system in claim 1, wherein the system specification is 1 standard deviation.

4. The system in claim 1, wherein the system specification is 2 standard deviations.

5. The system in claim 1, wherein the system specification is 3 standard deviations.

6. The system in claim 1, wherein the system specification is 4 standard deviations.

7. The system in claim 1, wherein the system specification is a Gaussian distribution.

8. The system in claim 1, wherein the system specification is a Poisson distribution.

9. The system in claim 1, wherein the light emitted is fluorescent.

10. The system of claim 1, wherein the light emitted is scattered.

11. The system in claim 1, wherein the data collection time windows are between about 80 to about 120 ADC points wide.

12. The system in claim 1, wherein the data collection time windows are between about 320 to about 360 ADC points wide.

13. The system in claim 1, wherein the diagnostic parameter relates to a fluid pressure.

14. The system in claim 1, wherein the diagnostic parameter relates to a mechanical perturbation in a pump.

15. The system in claim 1, wherein the diagnostic parameter relates to a particle arrival time.

16. The system in claim 1, wherein the diagnostic parameter relates to laminar flow stability.

17. The system in claim 1, wherein the computer processor is additionally configured to calculate a time delay based on the distribution of data intensity peak times in the second data collection time window.

18. The system in claim 17, wherein the time delay is calculated to modify the size of the second data collection time window.

19. The system in claim 17, wherein the time delay is calculated to shift the second data collection time window.

20. The system in claim 17, wherein the time delay is calculated to modify the size of and shift the second data collection time window.

\* \* \* \* \*